(12) United States Patent
Hadida Ruah et al.

(10) Patent No.: US 7,598,412 B2
(45) Date of Patent: Oct. 6, 2009

(54) MODULATORS OF ATP-BINDING CASSETTE TRANSPORTERS

(75) Inventors: Sara S. Hadida Ruah, San Diego, CA (US); Ashvani K. Singh, San Diego, CA (US); Mark T. Miller, San Diego, CA (US); Matthew Hamilton, Hackettstown, NJ (US); Peter D. J. Grootenhuis, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 477 days.

(21) Appl. No.: 10/961,485

(22) Filed: Oct. 8, 2004

(65) Prior Publication Data

US 2005/0148648 A1 Jul. 7, 2005

Related U.S. Application Data

(60) Provisional application No. 60/509,642, filed on Oct. 8, 2003.

(51) Int. Cl.
C07C 229/00 (2006.01)
C07C 233/00 (2006.01)

(52) U.S. Cl. .................. 560/42; 564/158; 564/176; 562/451

(58) Field of Classification Search .............. 560/42; 562/451
See application file for complete search history.

(56) References Cited

U.S. PATENT DOCUMENTS

| 5,281,714 | A | * | 1/1994 | Fobare et al. | 546/282.4 |
|---|---|---|---|---|---|
| 5,387,709 | A | * | 2/1995 | Lardy et al. | 558/388 |
| 6,632,836 | B1 | * | 10/2003 | Baker et al. | 514/539 |
| 6,908,934 | B2 | * | 6/2005 | Adams et al. | 514/325 |

FOREIGN PATENT DOCUMENTS

| GB | 874206 | | 8/1961 |
|---|---|---|---|
| WO | WO 01/47875 | * | 7/2001 |
| WO | WO 01/02373 | * | 11/2001 |
| WO | WO 03/042191 | * | 5/2003 |
| WO | WO 03/051877 | | 6/2003 |
| WO | WO 03/062248 | | 7/2003 |
| WO | WO 03/063797 | * | 8/2003 |

OTHER PUBLICATIONS

Singh et al. Bioorganic and Medicinal Chemistry Letters, 2005, 15(11), 2824-2828.*
Purchase et al. STN Abstaract of Bioorganic & Medicinal Chemistry (1997), 5(4), 739-747.*
Airapetyan et al. STN Abstract of Khimiya Geterotsiklicheskikh Soedinenii (1993), (5), 677-80.*
Markaryan et al. STN Abstract of Armyanskii Khimicheskii Zhurnal (1975), 28(10), 829-35.*
Ma et al. Journal of Biological Chemistry 2002, 277(40), 37235-37241.*
Clark, C.R., and etc., "Anticonvulsant Activity of Some 4-Aminobenzamides", J. Med. Chem., vol. 27, pp. 779-782, 1984.
Ma, T., and etc., "High-affinity Activators of Cystic Fibrosis Transmembrane Conductance Regulator (CFTR) Chloride Conductance Identified by High-throughput Screening", J. Bio. Chem., vol. 227, No. 40, pp. 37235-327241, 2002.
Purchase, T.S., and etc., "Inhibitors of Acyl-CoA: Cholesterol Acyltransferase: Novel Tri-substituted Ureas as Hypocholesterolemic Agents", Bioorg. Med. Chem., vol. 5, No. 5, pp. 739-747, 1997.
Harper, N.J. and etc., "1-(3,4-Dichlorobenzamidomethyl)cyclohexyldimethylamine and Related Compounds as Potential Analgesics", J. Med. Chem., vol. 17, No. 11, pp. 1188-1193, 1974.
Miao, S., and etc., "Benzamide Derivatives as Blockers of Kv1.3 Ion Channel", Bioorg. Med. Chem., vol. 13, pp. 1161-1164, 2003.
Mndzhoyan, A.L. and etc., "Isoquinoline Derivatives; IV. Synthesis of 1-Diphenylmethyl-4,6,7-substituted 1,2,3,4-Tetrahyroisoquinolines and Their Analogs", Institute of Fine Organic Chemistry, Academy of Sciences of the Armenian SSSR, Erevan. Translated from Khimiya Geterotsiklicheskikh Soedinenii, No. 12, pp. 1670-1673, 1970.

* cited by examiner

*Primary Examiner*—D. Margaret Seaman
*Assistant Examiner*—Nizal S Chandrakumar
(74) *Attorney, Agent, or Firm*—Nancy K. Brennan; Kumar Govindaswamy; Vertex Pharmaceuticals Incorporated

(57) ABSTRACT

The present invention provides compounds of Formula I useful as modulators of ABC transporter activity,

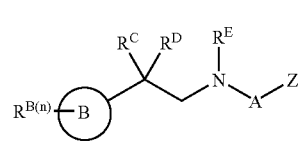

I or a pharmaceutically acceptable salt thereof, wherein $R^B$, n, B, $R^C$, $R^D$, $R^E$, A, and Z are described generally and in classes and subclasses below.

The present invention also provides pharmaceutical compositions, methods and kits associated with Formula I, useful for as modulators, and for the treatments of disease and disease conditions associated with ABC transporter proteins.

14 Claims, No Drawings

MODULATORS OF ATP-BINDING CASSETTE TRANSPORTERS

CROSS-REFERENCE TO RELATED APPLICATIONS

The present application claims the benefit under 35 U.S.C. § 119 of U.S. Provisional patent application No. 60/509,642, filed Oct. 8, 2003, the entire contents of the application being incorporated herein by reference.

TECHNICAL FIELD OF THE INVENTION

The present invention relates to modulators of ATP-Binding Cassette ("ABC") transporters or fragments thereof, including CF Transmembrane Regulator ("CFTR"), compositions thereof, and methods therewith. The present invention also relates to methods of treating ABC transporter mediated diseases using such modulators.

BACKGROUND OF THE INVENTION

ABC transporters are a group of membrane transporter proteins that play a major role in the transport and protection of cells against a wide variety of pharmacological agents, potentially toxic drugs, and xenobiotics. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. Up until the present time, 48 Human ABC Transporters have been identified, and these have been arranged into 7 families based on their sequence identity and function.

ABC transporters play a variety of important physiological roles within the body, as well as providing a defense against harmful compounds from the environment. Moreover they represent important potential drug targets both in their own right, as well as, because in many cases therapeutic drugs are also transported out of the target cell by these molecules.

One of the members of the ABC transporter family, namely, CFTR, is believed be the chloride channel responsible for cAMP-mediated chloride secretion in epithelial cells, and to play a key role in the secretion of chloride and maintenance of normal electrolyte transport throughout the body. CFTR is a protein of approximately 1480 amino acids made up of two repeated elements, each comprising six transmembrane segments and a nucleotide-binding domain. The two repeats are separated by a large, polar, regulatory (R)-domain containing multiple potential phosphorylation sites.

The gene associated with CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene leads to cystic fibrosis (hereinafter "CF"), the most common fatal genetic disease in humans affecting approximately one in every 2,500 infants born in the United States. Within the general United States population, up to 10 million people carry a single copy of the defective gene without apparent ill effects. In contrast, individuals with two copies of the CF associated gene suffer from the chronic effects of CF, including chronic lung destruction and death.

In patients with CF, expression of the CF associated gene in airway cells, leads to reduced cellular apical chloride conductance causing an imbalance in ion and fluid transport. It is widely believed that this leads to the abnormal mucus secretion in pancreatic ductules and in the airways that ultimately results in the pulmonary infections and epithelial cell damage typically associated with disease progression in CF. In addition to respiratory problems, CF patients typically suffer from gastrointestinal problems, and pancreatic insufficiency. Males are almost uniformly infertile and fertility is decreased in females. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). At present, more than 1000 mutations in the CF gene have been identified (http://www.genet.sickkids.on.ca/cftr/), but population studies have indicated that the most common CF mutation, a deletion of the 3 nucleotides that encode phenylalanine at position 508 of the CFTR amino acid sequence, is associated with approximately 70% of the cases of cystic fibrosis. The mutated CFTR protein is referred to as ΔF508.

It is believed that the deletion of residue 508 in ΔF508-CFTR prevents the nascent protein from folding correctly, resulting in the inability of this mutant protein to exit the endoplasmic reticulum (hereinafter "ER"), and traffic to the plasma membrane. As a result, insufficient amounts of the mature protein are present at the plasma membrane and chloride transport within epithelial tissues is significantly reduced (Quinton, P. M. (1990), FASEB J. 4: 2709-2727). Hence, the cellular phenomenon of defective ER processing of other proteins like CFTR, by the ER machinery, has been shown to be the underlying basis for a wide range of isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5 (7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. Studies have shown, however, that ΔF508-CFTR, when presented at the plasma membrane is functional as a cAMP-responsive Cl⁻ channel (Dalemans et al. (1991), Nature Lond. 354:526-528; Denning et al., supra.; Pasyk and Foskett (1995), J. Cell. Biochem. 270: 12347-50).

Although CFTR transports a variety of molecules in addition to anions, this role of transporting anions represents an important element in the overall cellular machinery for transporting ions and water across the epithelium. The other elements include the epithelial Na⁺ channel, ENaC, Na⁺/2Cl⁻/K⁺ co-transporter, Na⁺—K⁺-ATPase pump and the basolateral membrane K⁺ channels, that are responsible for the uptake of chloride into the cell.

These elements work together to achieve directional transport across the epithelium via their selective expression and localization within the cell. Chloride absorption takes place by the coordinated activity of: (i) ENaC and CFTR present on the apical membrane; and (ii) the Na⁺—K⁺-ATPase pump and Cl– channels expressed on the basolateral surface of the cell. Secondary active transport of chloride from the luminal side leads to the accumulation of intracellular chloride, which can then passively leave the cell via Cl⁻ channels, resulting in a vectorial transport. Arrangement of Na⁺/2Cl⁻/K⁺ co-transporter, Na$^+$—K$^+$-ATPase pump and the basolateral membrane K$^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to CF, modulation of CFTR activity may be beneficial for other diseases not directly caused by mutations in CFTR, such as secretory diseases and other protein folding diseases mediated by CFTR. These include, but are not limited to, chronic obstructive pulmonary disease (hereinafter "COPD"), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and to a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as CF and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms include dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5 (7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)].

The diseases associated with the first class of ER malfunction are CF (due to misfolded ΔF508-CFTR), hereditary emphysema (due to α1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to Vasopressin hormone/V2-receptor), neprogenic DI (due to aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as Spongiform encephalopathies, such as hereditary Creutzfeldt-Jakob disease (due to Prion protein processing defect), Fabry disease (due to lysosomal α-galactosidase A) and Straussler-Scheinker syndrome (due to Prp processing defect).

In CF, chloride transport mediated by the CFTR is reduced resulting in the abnormal mucus secretion that characterizes the disease. By contrast in secretory diarrheas epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, death and impaired growth.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). Sixteen million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E-coli* (ETEC) having the K99 pilus antigen. Common viral causes of diarrhea include rotavirus and coronavirus. Other infectious agents include cryptosporidium, *giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

There is a need for modulators that enhance the activity and/or function of CFTR in the plasma membrane.

SUMMARY OF THE INVENTION

It has now been found that compounds of this invention, and pharmaceutically acceptable compositions thereof, are useful as modulators of ABC transporter activity. These compounds have the general Formula I:

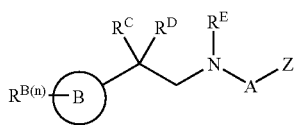

or a pharmaceutically acceptable salt thereof, wherein $R^B$, n, B, $R^C$, $R^D$, $R^E$, A, and Z are described generally and in classes and subclasses below.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease.

DETAILED DESCRIPTION OF THE INVENTION

1. Definitions

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111 (3), 477-90.

The term "CFTR" as used herein means cystic fibrosis transmembrane conductance regulator or a mutation thereof capable of regulator activity in part or full, including, but not limited to, ΔF508 CFTR and G551D CFTR (see, e.g., http://www.genet.sickkids.on.ca/cftr/, for CFTR mutations).

The term "COPD" as used herein means chronic obstructive pulmonary disease and comprises chronic obstructive bronchitis, and emphysema.

The term "modulating" as used herein means increasing or decreasing by a measurable amount.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic, bicyclic, or tricyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms, i.e., ((C1-C20)alkyl). In some embodiments, aliphatic groups contain 1-10 aliphatic carbon atoms, i.e., ((C1-C10)alkyl). In other embodiments, aliphatic groups contain 1-8 aliphatic carbon atoms, i.e., ((C1-C8)alkyl. In still other embodiments, aliphatic groups contain 1-6 aliphatic carbon atoms, i.e., ((C1-C6)alkyl, and in yet other embodiments aliphatic groups contain 1-4 aliphatic carbon atoms, i.e., ((C1-C4)alkyl. In some embodiments, "cycloaliphatic" (or "carbocycle" or "cycloalkyl") refers to a monocyclic C3-C8 hydrocarbon or bicyclic or tricyclic C8-C12 hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R$^\circ$; —OR$^\circ$; —SR$^\circ$; 1,2-methylene-dioxy; 1,2-ethylenedioxy; phenyl (Ph) optionally substituted with R$^\circ$; —O(Ph) optionally substituted with R$^\circ$; —(CH$_2$)$_{1-2}$(Ph), optionally substituted with R$^\circ$; —CH=CH(Ph), optionally substituted with R$^\circ$; —NO$_2$; —CN; —N(R$^\circ$)$_2$; —NR$^\circ$C(O)R$^\circ$; —NR$^\circ$C(O)N(R$^\circ$)$_2$; —NR$^\circ$CO$_2$R$^\circ$; —NR$^\circ$NR$^\circ$C(O)R$^\circ$; —NR$^\circ$NR$^\circ$C(O)N(R$^\circ$)$_2$; —NR$^\circ$NR$^\circ$CO$_2$R$^\circ$; —C(O)C(O)R$^\circ$; —C(O)CH$_2$C(O)R$^\circ$; —CO$_2$R$^\circ$; —C(O)R$^\circ$; —C(O)N(R$^\circ$)$_2$; —OC(O)N(R$^\circ$)$_2$; —S(O)$_2$R$^\circ$; —SO$_2$N(R$^\circ$)$_2$; —S(O)R$^\circ$; —NR$^\circ$SO$_2$N(R$^\circ$)$_2$; —NR$^\circ$SO$_2$R$^\circ$; —C(=S)N(R$^\circ$)$_2$; —C(=NH)—N(R$^\circ$)$_2$; or —(CH$_2$)$_{0-2}$NHC(O)R$^\circ$ wherein each independent occurrence of R$^\circ$ is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R$^\circ$, on the same substituent or different substituents, taken together with the atom(s) to which each R$^\circ$group is bound, form a 3- to 8-membered cycloalkyl, heterocyclyl, aryl, or heteroaryl ring having 0-3 heteroatoms independently selected from nitrogen, oxygen, or sulfur. Optional substituents on the aliphatic group of R$^\circ$are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R$^\circ$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C1-C4 aliphatic)$_2$, halogen, (C1-C4)aliphatic, OH, O((C1-C4)aliphatic), NO$_2$, CN, CO$_2$H, CO$_2$((C1-C4) aliphatic), O(halo(C1-C4)aliphatic), or halo((C1-C4)aliphatic), wherein each of the foregoing (C1-C4)aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R⁺ group is bound, form a 3- to 8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R⁺ are selected from $NH_2$, NH((C1-C4)aliphatic), N((C1-C4)aliphatic)$_2$, halogen, (C1-C4)aliphatic, OH, O((C1-C4)aliphatic), $NO_2$, CN, $CO_2H$, $CO_2$((C1-C4)aliphatic), O(halo(C1-C4)aliphatic), or halo((C1-C4)aliphatic), wherein each of the foregoing $C^{1-4}$aliphatic groups of R⁺ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R⁺, or any other variable similarly defined herein), are taken together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

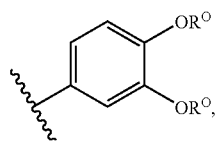

these two occurrences of R° are taken together with the oxygen atoms to which they are bound to form a fused 6-membered oxygen containing ring:

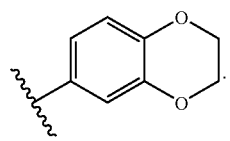

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

2. General Description of the Invention

The present invention relates to compounds of formula I:

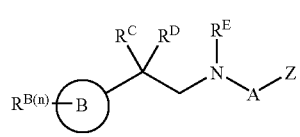

I or a pharmaceutically acceptable salt thereof, wherein:
 A is C(O), or $SO_2$;
 $R^C$ and $R^D$ are independently selected from H, (C1-C4) alkyl, and aryl, or may be taken together to form a (C3-C8)cycloalkyl or heterocyclic;
 $R^E$ is H, (C1-C4)alkyl optionally substituted with a substituent selected from CN, $NO_2$, $CF_3$, $OCF_3$, OH, $SR^6$, $S(O)R^6$, $SO_2R^6$, COOH, $COOR^6$, $OR^6$ or phenyl optionally substituted with $R^Z$;
 B is aryl or heterocyclic;

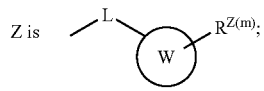

wherein,
 L is (C1-C6)alkylidene, —O—((C1-C6)alkylidene), ((C1-6)alkylidene)-O—, or a bond, wherein up to two carbon atoms in said alkylidene in L are independently replaced with O, S, or N;
 W is aryl, heterocyclic, or (C5-C7)cycloalkyl;
 m and n are independently 0 to 5; and
 $R^B$ and $R^Z$ are independently selected from $R^1$, $R^2$, $R^3$, $R^4$, or $R^5$, wherein:
 $R^1$ is oxo, $R^6$ or $((C1-C4)aliphatic)_n$—Y;
 n is 0 or 1;
 Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, $N(R^8)_2$, COOH, $COOR^6$ or $OR^6$; or two $R^1$ on adjacent ring atoms, taken together, form 1,2-methylenedioxy or 1,2-ethylenedioxy;
 $R^2$ is aliphatic, wherein each $R^2$ optionally comprises up to 2 substituents independently selected from $R^1$, $R^4$, or $R^5$;
 $R^3$ is a cycloaliphatic, aryl, heterocyclic, or heteroaryl ring optionally comprising up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^5C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^5SO_2R^6$, $NR^6SO_2N(R^6)_2$, $NR^5SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;

$R^5$ is a cycloaliphatic, aryl, heterocyclic, or heteroaryl ring, optionally comprising up to 3 $R^1$ substituents;

$R^6$ is H or aliphatic, wherein $R^6$ optionally comprises a $R^7$ substituent;

$R^7$ is a cycloaliphatic, aryl, heterocyclic, or heteroaryl ring, and each $R^7$ optionally comprises up to 2 substituents independently chosen from H, $(C_1-C_6)$-straight or branched alkyl, $(C_2-C_6)$ straight or branched alkenyl or alkynyl, 1,2-methylenedioxy, 1,2-ethylenedioxy, or $(CH_2)_n$-Q;

Q is selected from halo, CN, $NO_2$, $CF_3$, $OCF_3$, OH, S-aliphatic, S(O)-aliphatic, $SO_2$-aliphatic, $NH_2$, NH(aliphatic), N(aliphatic)$_2$, N(aliphatic)$R^8$, $NHR^8$, $N(R^8)_2$, COOH, C(O)O-(aliphatic), or O-aliphatic; and $R^8$ is an amino protecting group.

The term "amino protecting group" refers to a suitable chemical group that may be attached to a nitrogen atom. The term "protecting" refers to when the designated amino group is attached to a suitable chemical group (e.g., capping group). Examples of suitable amino capping groups are described in T. W. Greene et al., *Protective Groups in Organic Synthesis*, 3d. Ed., John Wiley and Sons (1999); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

In certain other embodiments in the compounds of formula I:

a) when A is C(O), L is a bond, Z is phenyl, $R^C$ and $R^D$ taken together is cyclopentyl, B is phenyl, then $R^B$ and $R^Z$ are not methoxy;

b) when A is C(O), L is a bond, Z is phenyl, $R^C$ and $R^D$ taken together is cyclopropyl, B is phenyl, then $R^B$ is not hydrogen;

c) when A is C(O), L is a bond, Z is benzofuranyl, $R^C$ and $R^D$ taken together is cyclopentyl, B is phenyl, then $R^B$ is not methoxy;

d) when A is C(O), L is a bond, Z is phenyl, $R^C$ and $R^D$ taken together is cyclopentyl, B is phenyl, $R^B$ is hydrogen, then $R^Z$ is not chloro;

e) when A is C(O), L is a bond, Z is furanyl, $R^C$ and $R^D$ taken together is cyclopentyl, B is phenyl, $R^B$ is methoxy, then $R^Z$ is not bromo;

f) when A is C(O), L is a bond, Z is furanyl, $R^C$ and $R^D$ taken together is cyclopentyl, B is phenyl, then $R^B$ is not hydrogen; and g) when A is C(O), L is a bond, Z is phenyl, $R^C$ and $R^D$ taken together is cyclohexyl, B is phenyl, $R^B$ is methoxy, n is 2, $R^Z$ is nitro, then m is not 2.

In certain embodiments of compounds of the present invention, when $R^C$ and $R^D$ each is methyl, $R^E$ is hydrogen, and A is carbonyl, then the following compounds are excluded:

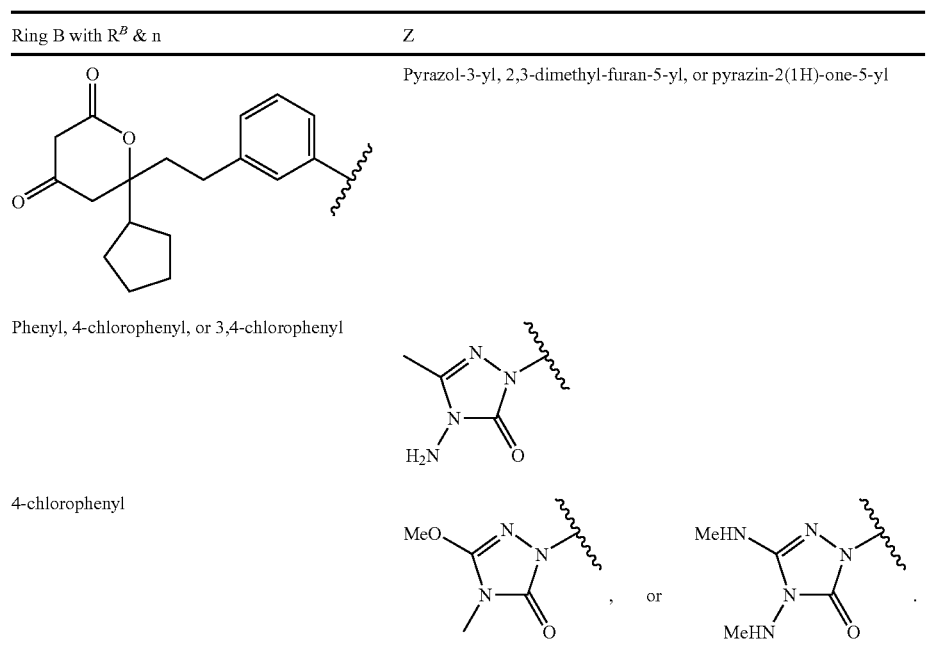

In an alternative embodiment, the present invention provides a compound of formula II:

$$\text{R}^{B(n)} \overset{}{\underset{}{\text{B}}} \overset{\text{R}^C \; \text{R}^D}{\underset{}{\text{C}}} \overset{\text{R}^E}{\underset{}{\text{N}}} \overset{}{\underset{\text{A}}{}} Z$$
II or a pharmaceutically acceptable salt thereof, wherein:
  A is C(O) or SO$_2$;
  R$^C$ and R$^D$ taken together form a 3-6 membered cycloalkyl ring or 4-pyranyl ring;
  R$^E$ is H, (C1-C4)alkyl optionally substituted with a substituent selected from (C1-C4)alkyl selected CN, NO$_2$, CF$_3$, OCF$_3$, OH, SR$^6$, S(O)R$^6$, SO$_2$R$^6$, COOH, COOR$^6$, OR$^6$ or phenyl optionally substituted with R$^Z$;
  B is phenyl;

Z is $\overset{}{\underset{}{}} \overset{\text{L}}{\underset{}{}} \overset{}{\underset{\text{W}}{}} \text{R}^{Z(m)}$;

wherein,
  L is a bond;
  W is a 5-14 membered monocyclic, bicyclic, or tricyclic heterocyclic or heteroaryl ring;
  m and n are independently 0 to 5; or
  Z is diphenylmethyl wherein each phenyl has up to 5 R$^Z$ is substituents; and
  R$^B$ and R$^Z$ are independently selected from R$^1$, R$^2$, R$^3$, R$^4$, or R$^5$, wherein:
    R$^1$ is oxo, R$^6$ or ((C1-C4)aliphatic)$_n$-Y;
    n is 0 or 1;
    Y is halo, CN, NO$_2$, CF$_3$, OCF$_3$, OH, SR$^6$, S(O)R$^6$, SO$_2$R$^6$, NH$_2$, NHR$^6$, N(R$^6$)$_2$, NR$^6$R$^8$, COOH, COOR$^6$ or OR$^6$; or two R$^1$ on adjacent ring atoms, taken together, form 1,2-methylenedioxy or 1,2-ethylenedioxy;
  R$^2$ is aliphatic, wherein each R$^2$ optionally comprises up to 2 substituents independently selected from R$^1$, R$^4$, or R$^5$;
    R$^3$ is a cycloaliphatic, aryl, heterocyclic, or heteroaryl ring optionally comprising up to 3 substituents, independently selected from R$^1$, R$^2$, R$^4$ or R$^5$;
    R$^4$ is OR$^5$, OR$^6$, OC(O)R$^6$, OC(O)R$^5$, OC(O)OR$^6$, OC(O)OR$^5$, OC(O)N(R$^6$)$_2$, OC(O)N(R$^5$)$_2$, OC(O)N(R$^6$R$^5$), SR$^6$, SR$^5$, S(O)R$^6$, S(O)R$^5$, SO$_2$R$^6$, SO$_2$R$^5$, SO$_2$N(R$^6$)$_2$, SO$_2$N(R$^5$)$_2$, SO$_2$NR$^5$R$^6$, SO$_3$R$^6$, SO$_3$R$^5$, C(O)R$^5$, C(O)OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^6$, C(O)N(OR$^5$)R$^6$, C(O)N(OR$^6$)R$^5$, C(O)N(OR$^5$)R$^5$, C(NOR$^6$)R$^6$, C(NOR$^6$)R$^5$, C(NOR$^5$)R$^6$, C(NOR$^5$)R$^5$, N(R$^6$)$_2$, N(R$^5$)$_2$, N(R$^5$R$^6$), NR$^5$C(O)R$^5$, NR$^6$C(O)R$^6$, NR$^5$C(O)R$^6$, NR$^6$C(O)R$^5$, NR$^6$C(O)OR$^6$, NR$^5$C(O)OR$^6$, NR$^6$C(O)OR$^5$, NR$^5$C(O)OR$^5$, NR$^6$C(O)N(R$^6$)$_2$, NR$^6$C(O)NR$^5$R$^6$, NR$^6$C(O)N(R$^5$)$_2$, NR$^5$C(O)N(R$^6$)$_2$, NR$^5$C(O)NR$^5$R$^6$, NR$^5$C(O)N(R$^5$)$_2$, NR$^6$SO$_2$R$^6$, NR$^6$SO$_2$R$^5$, NR$^5$SO$_2$R$^5$, NR$^5$SO$_2$R$^6$, NR$^6$SO$_2$N(R$^6$)$_2$, NR$^5$SO$_2$N(R$^6$)$_2$, NR$^6$SO$_2$NR$^5$R$^6$, NR$^6$SO$_2$N(R$^5$)$_2$, NR$^5$SO$_2$NR$^5$R$^6$, NR$^5$SO$_2$N(R$^5$)$_2$, N(OR$^6$)R$^6$, N(OR$^6$)R$^5$, N(OR$^5$)R$^5$, or N(OR$^5$)R$^6$;

R$^5$ is a cycloaliphatic, aryl, heterocyclic, or heteroaryl ring, optionally comprising up to 3 R$^1$ substituents;

R$^6$ is H or aliphatic, wherein R$^6$ optionally comprises a R$^7$ substituent;

R$^7$ is a cycloaliphatic, aryl, heterocyclic, or heteroaryl ring, and each R$^7$ optionally comprises up to 2 substituents independently chosen from H, (C$_1$-C$_6$)-straight or branched alkyl, (C$_2$-C$_6$) straight or branched alkenyl or alkynyl, 1,2-methylenedioxy, 1,2-ethylenedioxy, or (CH$_2$)$_n$-Q;

Q is selected from halo, CN, NO$_2$, CF$_3$, OCF$_3$, OH, S-aliphatic, S(O)-aliphatic, SO$_2$-aliphatic, NH$_2$, NH(aliphatic), N(aliphatic)$_2$, N(aliphatic)R$^8$, NHR$^8$, N(R$^8$)$_2$, COOH, C(O)O-(aliphatic), or O-aliphatic; and R$^8$ is an amino protecting group, provided that:
(i) when R$^C$ and R$^D$ taken together form a 4-pyran ring, R$^E$ is hydrogen, A is C(O), and ring W together with R$^Z$ and m is 2-amino-pyrazin-3-yl, then ring B together with (R$^B$)$_n$ is not phenyl, 4-methylphenyl, 4-chlorophenyl, 3-fluorophenyl, 4-methoxyphenyl, 2,4-difluorophenyl, or 4-fluorophenyl;
(ii) when R$^C$ and R$^D$ taken together form a cyclohexyl ring, R$^E$ is hydrogen, A is C(O), and L is 2-methoxy-pyridin-3-yl, then ring B together with (R$^B$)$_n$ is not phenyl;
(iii) when R$^C$ and R$^D$ taken together form a cyclobutyl ring, R$^E$ is hydrogen, A is C(O), and ring W together with R$^Z$ and m is 2,5,7,8-tetramethyl-6-hydroxy-2H-1-benzopyran-2-yl, then ring B together with (R$^B$)$_n$ is not 4-[(imino-thien-2-ylmethyl)amino]phenyl;
(iv) when R$^C$ and R$^D$ taken together form a cyclopropyl ring, R$^E$ is hydrogen, A is C(O), and ring W together with R$^Z$ and m is 2,5-dihydro-4-hydroxy-1-methyl-5-oxo-1H-pyrrol-3-yl, then ring B together with (R$^B$)$_n$ is not phenyl;
(v) when R$^C$ and R$^D$ taken together form a cyclopropyl ring, R$^E$ is hydrogen, A is C(O), and ring W together with R$^Z$ and m is 2,3,4,9-tetrahydro-3-[(3'-(2,6-diisopropyl)-ureido]-1H-carbazol-3-yl, then ring B together with (R$^B$)$_n$ is not 4-chlorophenyl;
(vi) when R$^C$ and R$^D$ taken together form a cyclopropyl ring, R$^E$ is hydrogen, A is C(O), and ring W together with R$^Z$ and m is 9,10-dihydro-9-oxo-acridin-3-yl, then ring B together with (R$^B$)$_n$ is not 4-chlorophenyl;
(vii) when R$^E$ is hydrogen and A is C(O), then the following compounds are excluded:

| $R^C$ & $R^D$ together | ring W together with $R^2$ and m | ring B with $R^B$ & n |
|---|---|---|
| 4-pyran | ![structure: 7-morpholino-4-methoxy-benzothiazol-2-yl] | phenyl |
| 4-pyran | diphenylmethyl | phenyl |
| cyclobutyl | ![structure: 2,3-dichloro-4H-thieno[3,2-b]pyrrol-5-yl] | phenyl |
| cyclopentyl | benzofuran-2-yl | 3,4-dimethoxyphenyl |
| cyclopropyl | ![structure: 1-(2-morpholinoethyl)-7-methoxy-indazol-3-yl] | 4-chlorophenyl |
| cyclopropyl | ![structure: 9-(3-phenylpropyl)-9H-xanthen-9-yl] | phenyl |
| 4-pyran or cyclohexyl | diphenylmethyl | 3,4-dimethoxyphenyl |
| 4-pyran | 2-furanyl | 4-methoxyphenyl |
| 4-pyran | 5-bromo-2-furanyl | phenyl |
| cyclopentyl | ![structure: 7-methyl-thieno[2,3-b]quinolin-2-yl] | phenyl |
| 4-pyran | 1,4-benzodioxin-2-yl | phenyl |
| 4-pyran | 4,5-dimethyl-furan-2-yl | phenyl |
| cyclohexyl | benzofuran-2-yl | 3,4-dimethoxyphenyl |
| cyclopentyl | diphenylmethyl | 3,4-dimethoxyphenyl |
| cyclopentyl | ![structure: 2-isobutyl-9-methyl-1-oxo-2,9-dihydro-1H-β-carbolin-4-yl] | phenyl |

| $R^C$ & $R^D$ together | ring W together with $R^2$ and m | ring B with $R^B$ & n |
|---|---|---|
| cyclopentyl | 5-bromo-furan-2-yl | 3,4-dimethoxyphenyl |
| cyclopentyl | 7-methoxy-thieno[2,3-b]quinolin-2-yl (structure) | phenyl |
| 4-pyran | 2-furanyl, 5-ethyl-furan-2-yl, 2-thienyl, | phenyl |
| cyclopentyl | 2-(1-methyl-1H-indol-3-yl)-2-methyl-1-oxo-1,2,3,4-tetrahydroisoquinolin-4-yl (structure) or 2-[2-(4-methoxyethyl)]-3-(1-methyl-1H-indol-3-yl)-1-oxo-1,2,3,4-tetrahydroisoquinolin-4-yl (structure) | phenyl |
| 4-pyranyl | 2-benzofuranyl | phenyl |
| 4-pyranyl | 5-bromofuran-2-yl | 4-methoxyphenyl |
| cyclopentyl | 5-bromofuran-2-yl | phenyl |
| 4-pyranyl | 2-thienyl | 4-methoxyphenyl |
| 4-pyranyl | diphenylmethyl | 4-methoxyphenyl |
| cyclopentyl | 2-benzofuranyl | phenyl |
| 4-pyranyl | 2-benzofuranyl | 3,4-dimethoxyphenyl |
| cyclopentyl | 1-phenyl-1-(4-isobutoxy-phenyl)-methyl | phenyl |
| cyclopentyl | 1,4-benzodioxin-2-yl | 3,4-dimethoxyphenyl |

(viii) when $R^C$ and $R^D$ taken together form a cyclopentyl ring, $R^E$ is hydrogen, A is C(O), and ring W together with $R^Z$ and m is diphenylmethyl, then ring B together with $(R^B)_n$ is not phenyl, 4-ethoxyphenyl, 4-butoxyphenyl, 4-isobutoxyphenyl, or 4-methoxyphenyl.

In one embodiment of the present invention, A is C(O) Or, A is $SO_2$.

In one embodiment, $R^E$ is hydrogen. Or, $R^E$ is C1-C4 alkyl.

In another embodiment, $R^C$ and $R^D$, taken together, form a 4-pyranyl ring.

In another embodiment, $R^C$ and $R^D$, taken together, form a 3-6 membered cycloalkyl ring. In one embodiment, $R^C$ and $R^D$, taken together, form a 5-6 membered cycloalkyl ring.

In another embodiment, $R^C$ and $R^D$, taken together, form a 5-membered cycloalkyl ring. Or, $R^C$ and $R^D$, taken together, form a 6-membered cycloalkyl ring.

In another embodiment, W is an optionally substituted indolyl, benzofuranyl, or benzothienyl. Or, W is is indol-2-yl or indol-3-yl. Or W is benzofuran-2-yl. Or, W is benzothien-2-yl.

In another embodiment, W is an optionally substituted pyrazolyl or indazolyl.

In another embodiment, W is an optionally substituted pyrazol-3-yl or pyrazol-4-yl. Or, W is an optionally substituted indazol-3-yl.

In another embodiment, W is an optionally substituted phenyl.

In another embodiment, W is an optionally substiuted six-membered heteroaromatic ring having up to three heteroatoms selected from O, S, or N. In certain embodiments, W is pyridyl.

In another embodiment, Z is diphenylmethyl.

In certain embodiments, W is an optionally substituted ring selected from furanyl, thienyl, isoxazolyl, or pyrrolyl.

In another embodiment, W is an optionally substituted 10-12 membered bicyclic, heteroaromatic ring. In certain embodiments, W is an optionally substituted ring selected from quinolinyl or cinnolinyl.

In one embodiment of the present invention, $R^C$ and $R^D$ each is methyl.

According to a preferred embodiment, $R^8$ is acetyl, arylsulfonyl or alkylsulfonyl.

Another embodiment of the present invention provides a method of treating an ABC transporter mediated disease in a mammal, comprising the step of administering to said mammal a composition comprising a compound of the present invention or a pharmaceutically acceptable salt thereof.

A preferred aspect of the present embodiment is where the ABC transporter mediated disease is selected from cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/Pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, progressive supranuclear plasy, Pick's disease, several polyglutamine neurological disorders asuch as Huntington, Spinocerebullar ataxia type I, spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker syndrome, COPD, dry eye disease, or Sjögren's disease.

An especially preferred method is where the disease is CF.

Another embodiment of the present invention provides a pharmaceutical composition comprising:

a. a compound of the present invention;

b. a pharmaceutically acceptable carrier; and c. an additional agent selected from a mucolytic agent, bronchodialator, an antibiotic, an anti-infective agent, an anti-inflammatory agent, CFTR modulator other than a compound of the present invention, or a nutritional agent.

Another embodiment of the present invention provides a method of modulating ABC transporter activity, comprising the step of contacting said ABC transporter with a compound of the present invention.

A preferred aspect of this embodiment is where the ABC transporter or a fragment thereof is in vivo. Another preferred aspect of this embodiment is where the ABC transporter or a fragment thereof is in vitro. Another preferred aspect of this embodiment is where the ABC transporter is CFTR.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity.

According to a preferred embodiment, said functional ABC transporter is CFTR.

Another embodiment of the present invention provides a kit for use in measuring the activity of a ABC transporter or a fragment thereof in a biological sample in vitro or in vivo, comprising:

a. a composition comprising a compound of the present invention; and b. instructions for:

i) contacting said composition with the biological sample; and ii) measuring activity of said ABC transporter or fragment thereof.

A preferred aspect of this embodiment is where the ABC transporter is CFTR.

3. Description of Exemplary Compounds

As described generally above, for compounds of the invention, $R^C$ and $R^D$ are independently selected from H, $C_{1-4}$alkyl, and aryl, or may be taken together to form a (C3-C8)cycloalkyl; B is aryl; and Z is (C1-C6)alkyl, aryl, (C1-C4alkyl) aryl, C5-C7cycloalkyl, or ((C1-4)alkyl) $C_{5-7}$cycloalkyl.

A preferred embodiment of the present invention is where A is C(O), and L is a bond.

A preferred embodiment of the present invention is where $R^C$ and $R^D$ taken together form (C3-C8)cycloalkyl.

A particularly preferred embodiment of the present invention is where $R^C$ and $R^D$ taken together form cyclopentyl.

Another particularly preferred embodiment of the present invention is where $R^C$ and $R^D$ taken together form cyclohexyl.

A preferred embodiment of the present invention is where $R^C$ and $R^D$ taken together form a heterocyclic.

A particularly preferred embodiment of the present invention is where $R^C$ and $R^D$ taken together form pyranyl. In certain embodiments, $R^C$ and $R^D$ taken together form 4-pyranyl.

Yet another particularly preferred embodiment of the present invention is where $R^C$ and $R^D$ are H.

Yet another particularly preferred embodiment of the present invention is where $R^C$ and $R^D$ are methyl.

A preferred embodiment of the present invention is where B is aryl.

A particularly preferred embodiment of the present invention is where B is phenyl.

A preferred embodiment of the present invention is where Z is aryl.

Another preferred embodiment of the present invention is where Z is pyridinyl.

Another preferred embodiment of the present invention is where Z is phenyl.

Another preferred embodiment of the present invention is where Z is benzofuran.

Another preferred embodiment of the present invention is where Z is benzothiophenyl.

Another preferred embodiment of the present invention is where Z is indolyl.

Another preferred embodiment of the present invention is where Z is pyrazolyl.

Another preferred embodiment of the present invention is where Z is furanyl.

Another preferred embodiment of the present invention is where Z is quinolinyl.

Another preferred embodiment of the present invention is where Z is isoquinolinyl.

Another preferred embodiment of the present invention is where Z is is cinnolinyl.

An especially preferred embodiment of the present invention is where Z is benzofuranyl, and $R^C$ and $R^D$ taken together form cyclohexyl.

Another especially preferred embodiment is where B is a substituted phenyl.

An especially preferred embodiment of the present invention is a compound where Z is benzofuranyl, $R^C$ and $R^D$ taken together form cyclohexyl, and B is a substituted phenyl as represented by formula II:

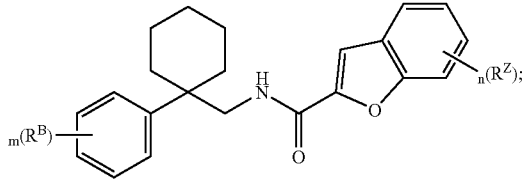

III or a pharmaceutically acceptable salt thereof;

wherein:
$R^Z$ is independently selected from (C1-C4)alkyl, (C1-C4) alkoxy, and halo, particularly methyl, methoxy, F, or Cl;
n is 0 to 4;
$R^B$ is independently selected from halo, and (C1-C4) alkoxy; and
m is 0 to 5.

In a preferred embodiment of the compound of formula III, m is 3, and $R^B$ is fluoro or a methoxy moiety. Exemplary compounds of the present invention are shown below in Table 1:

TABLE 1

| Cmpd # | Compound |
|---|---|
| 1 | |
| 2 | |
| 3 | |
| 4 | |
| 5 | |

TABLE 1-continued

| Cmpd # | Compound |
|---|---|
| 6 | *N-{[1-(3,4-dimethoxyphenyl)cyclopentyl]methyl}-4-fluorobenzamide* |
| 7 | *N-{[1-(3,4-dimethoxyphenyl)cyclopentyl]methyl}-1-benzofuran-2-carboxamide* |
| 8 | *N-[(1-phenylcyclopentyl)methyl]furan-2-carboxamide* |
| 9 | *N-(2-phenylethyl)-1-benzofuran-2-carboxamide* |
| 10 | *N-{[1-(3,4-dimethoxyphenyl)cyclopentyl]methyl}benzamide* |
| 11 | *3,4-dimethoxy-N-[(1-phenylcyclopentyl)methyl]benzamide* |

TABLE 1-continued
| Cmpd # | Compound |
|---|---|
| 12 | 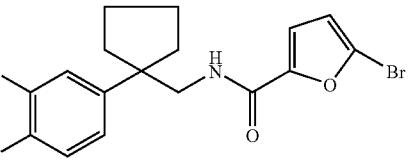 |
| 13 | 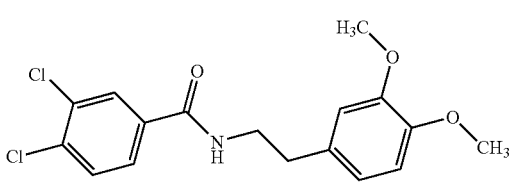 |
| 14 | 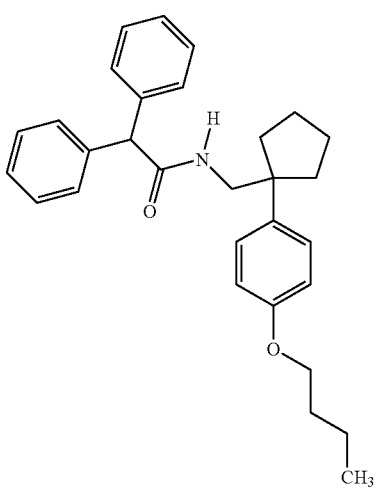 |
| 15 | 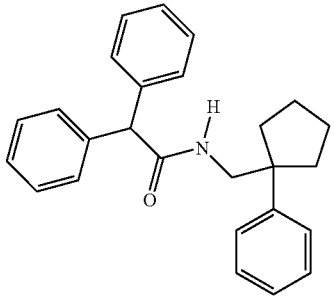 |
| 16 | 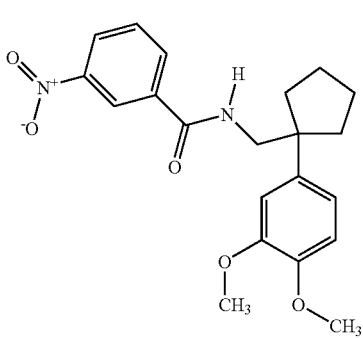 |

TABLE 1-continued
| Cmpd # | Compound |
|---|---|
| 17 | 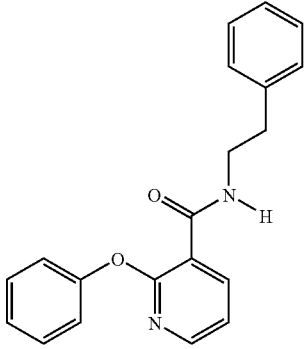 |
| 18 | 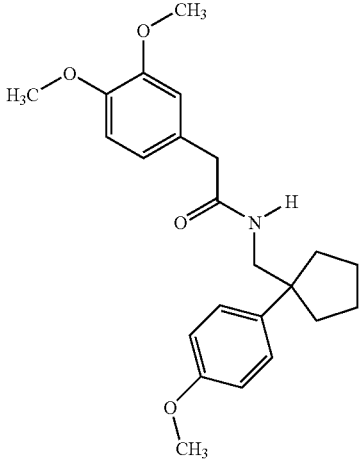 |
| 19 | 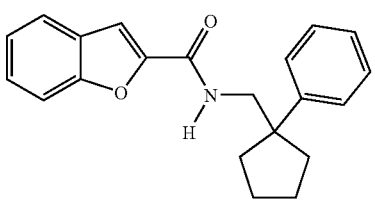 |
| 20 | 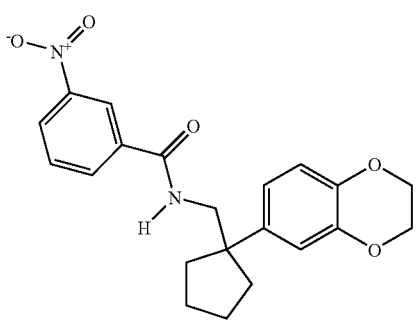 |

TABLE 1-continued
| Cmpd # | Compound |
|---|---|
| 21 | 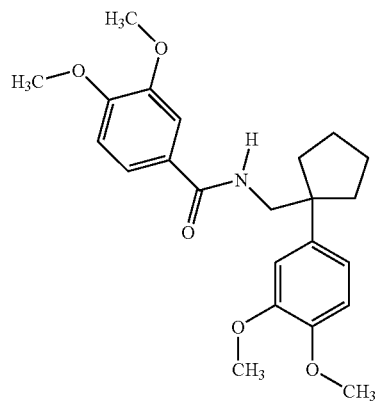 |
| 22 | 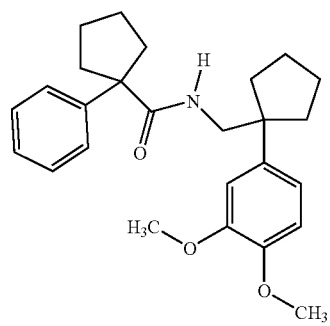 |
| 23 | 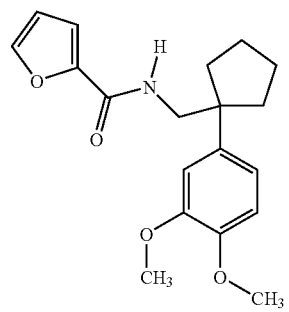 |
| 24 | 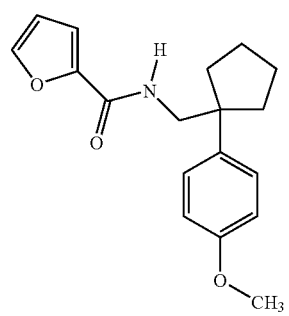 |

TABLE 1-continued

| Cmpd # | Compound |
|---|---|
| 25 | |
| 26 | |
| 27 | |
| 28 | |
| 29 | |

TABLE 1-continued
| Cmpd # | Compound |
|---|---|
| 30 | 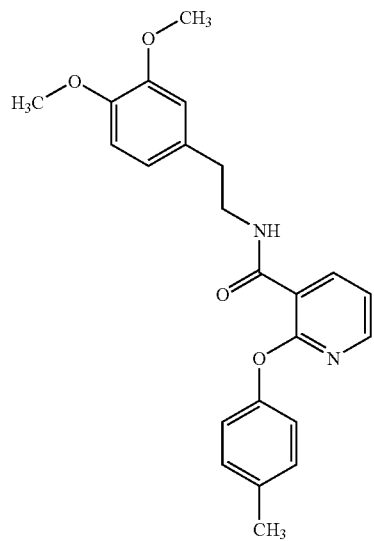 |
| 31 | 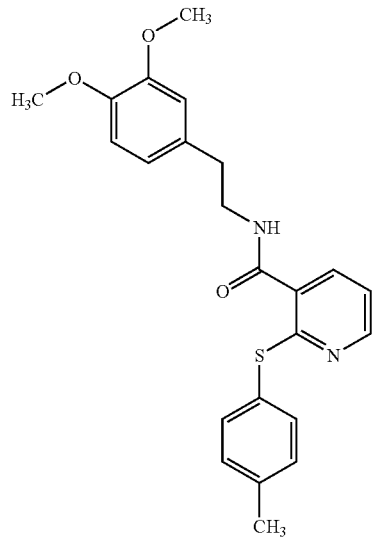 |
| 32 | 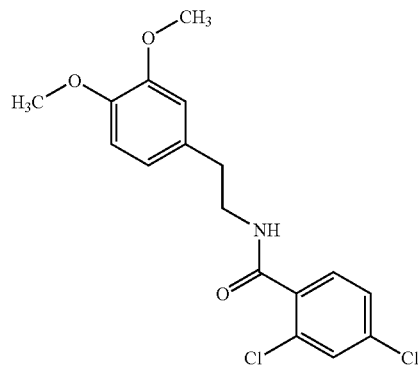 |

TABLE 1-continued

| Cmpd # | Compound |
|---|---|
| 33 | |
| 34 | |
| 35 | |
| 36 | |

TABLE 1-continued
| Cmpd # | Compound |
|---|---|
| 37 | 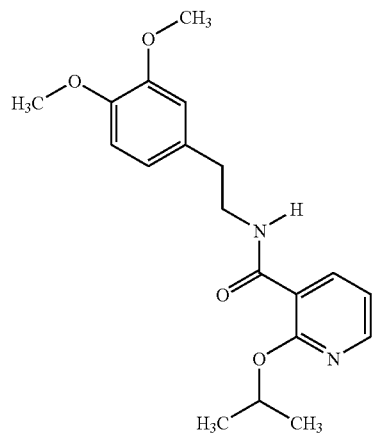 |
| 38 | 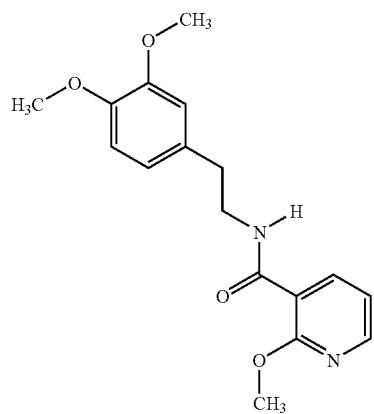 |
| 39 | 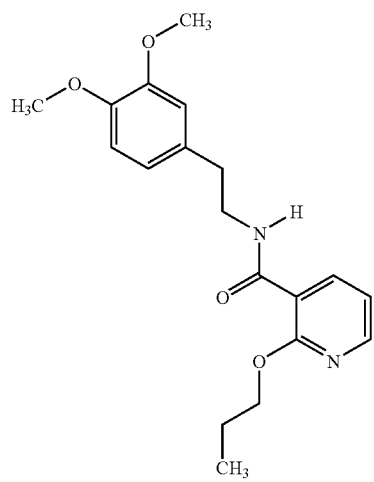 |

TABLE 1-continued
| Cmpd # | Compound |
|---|---|
| 40 | 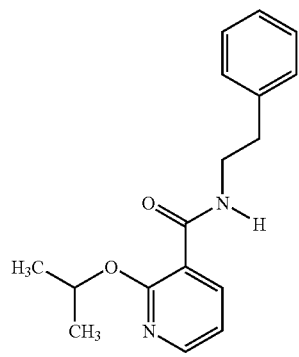 |
| 41 | 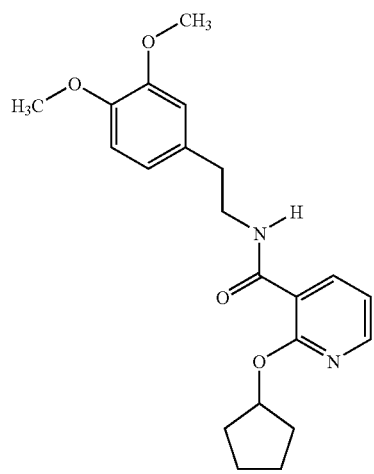 |
| 42 | 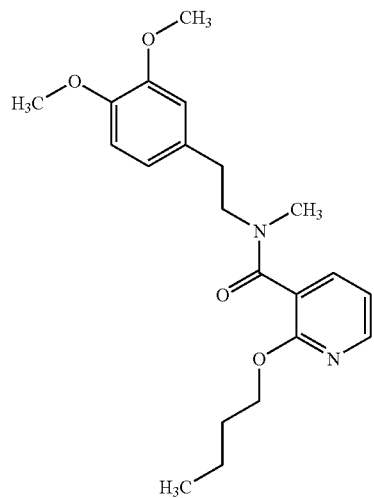 |

TABLE 1-continued
| Cmpd # | Compound |
|---|---|
| 43 | 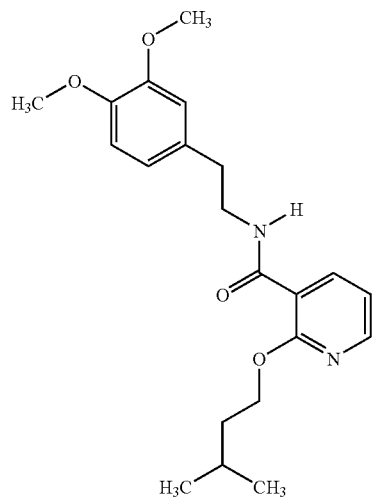 |
| 44 | 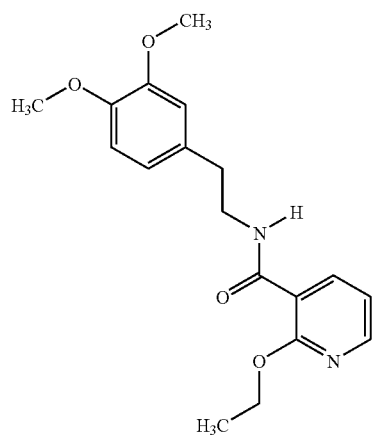 |
| 45 | 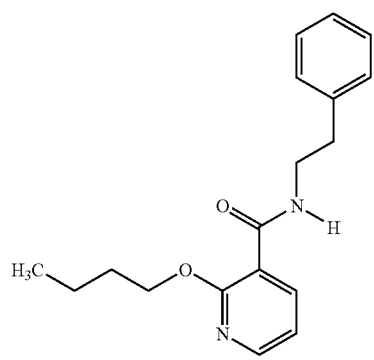 |

TABLE 1-continued
| Cmpd # | Compound |
|---|---|
| 46 | 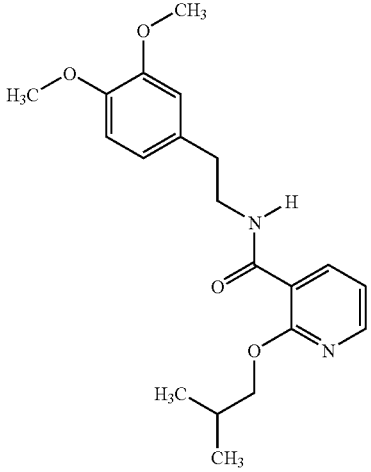 |
| 47 | |
| 48 | 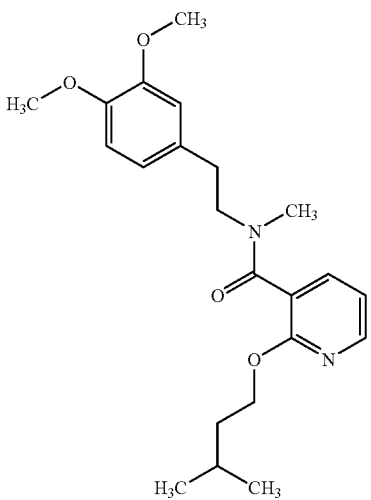 |

TABLE 1-continued
| Cmpd # | Compound |
|---|---|
| 49 | 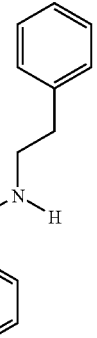 |
| 50 | 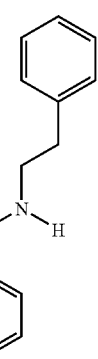 |
| 51 | 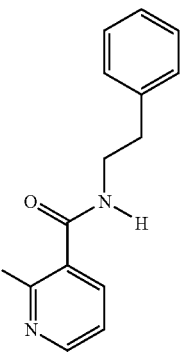 |
| 52 | 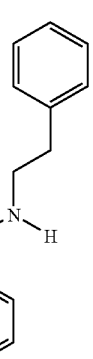 |

TABLE 1-continued
| Cmpd # | Compound |
|---|---|
| 53 | 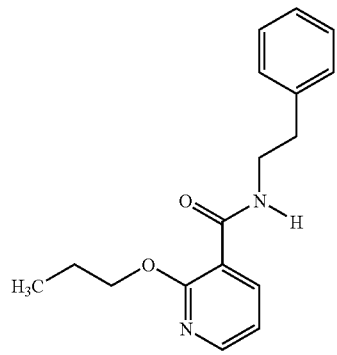 |
| 54 | 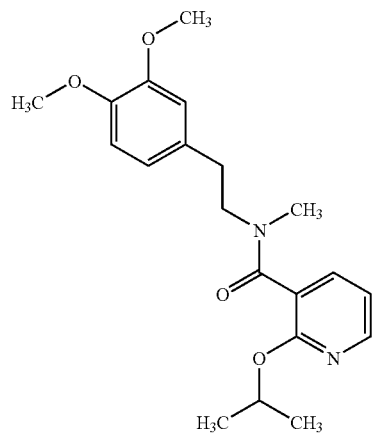 |
| 55 | 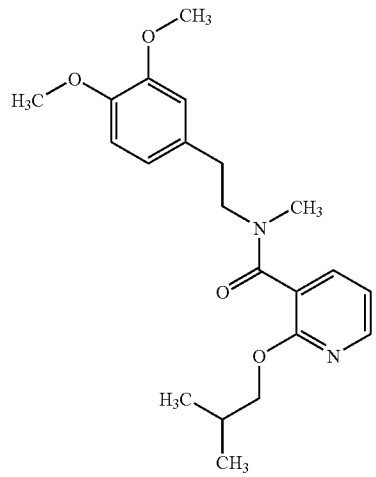 |

TABLE 1-continued
| Cmpd # | Compound |
|---|---|
| 56 | 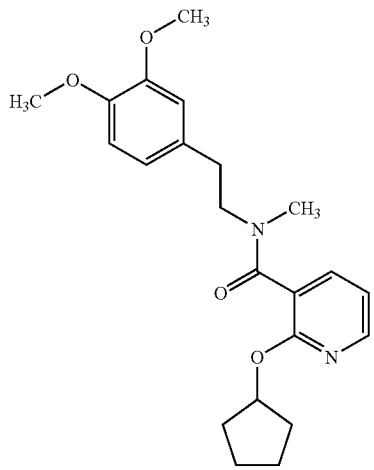 |
| 57 | 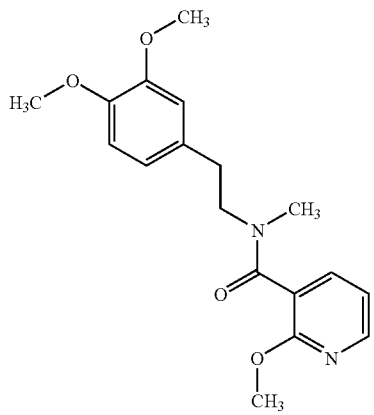 |
| 58 | 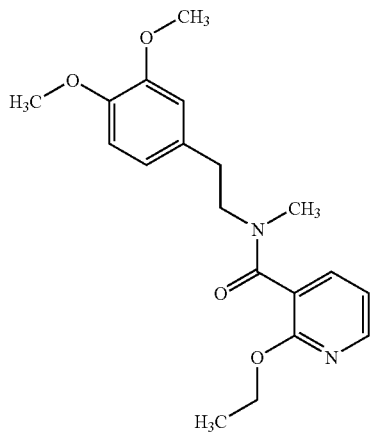 |

TABLE 1-continued
| Cmpd # | Compound |
|---|---|
| 59 | 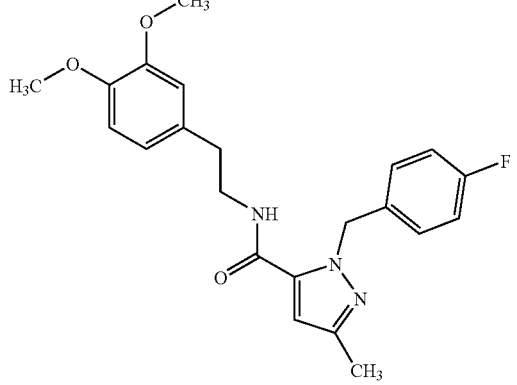 |
| 60 | 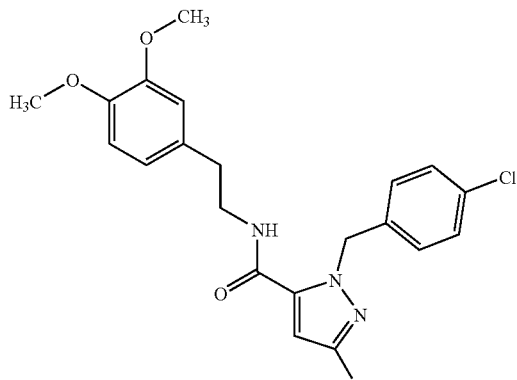 |
| 61 | 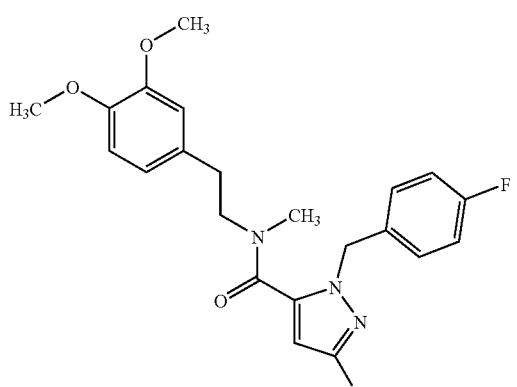 |

TABLE 1-continued
| Cmpd # | Compound |
|---|---|
| 62 | 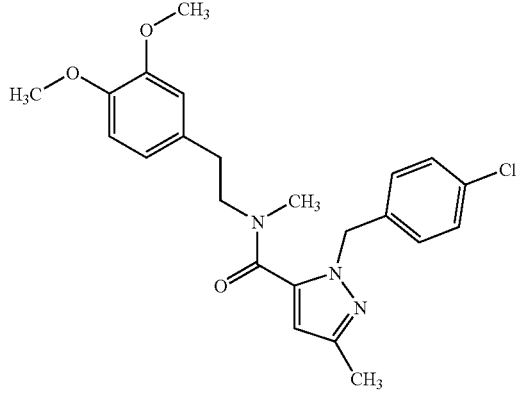 |
| 63 | 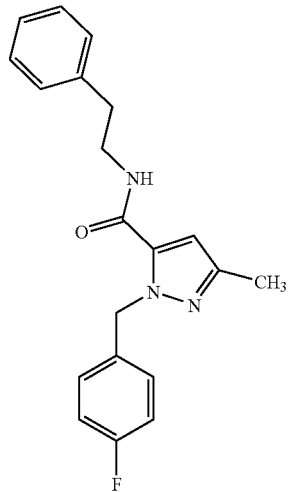 |
| 64 | 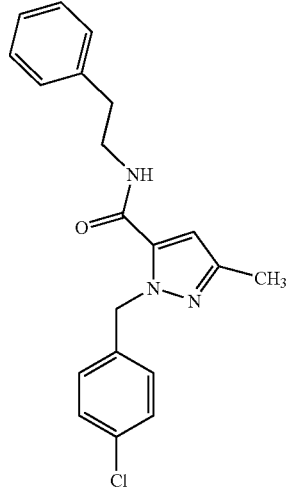 |

TABLE 1-continued
| Cmpd # | Compound |
|---|---|
| 65 | 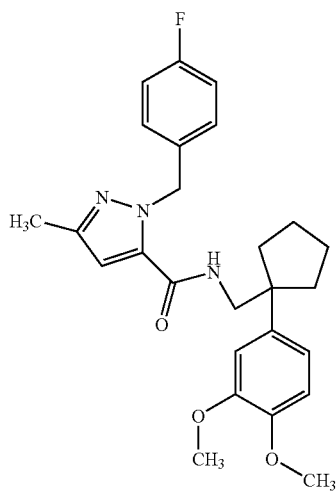 |
| 66 | 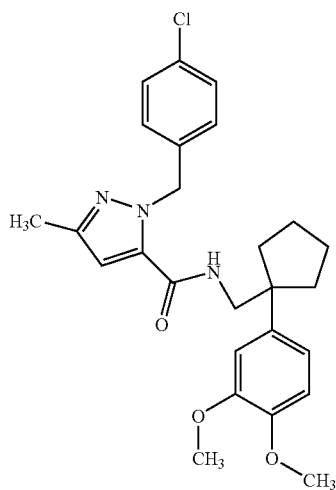 |
| 67 | 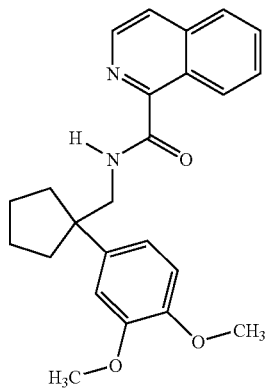 |

TABLE 1-continued
| Cmpd # | Compound |
| --- | --- |
| 68 | 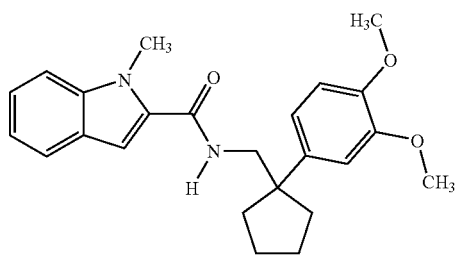 |
| 69 | 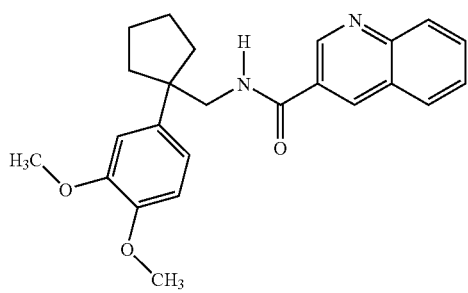 |
| 70 | 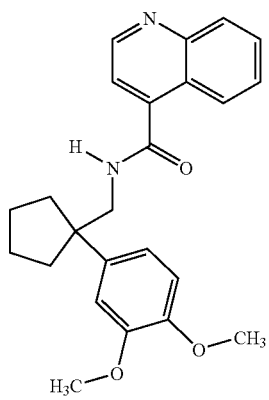 |
| 71 | 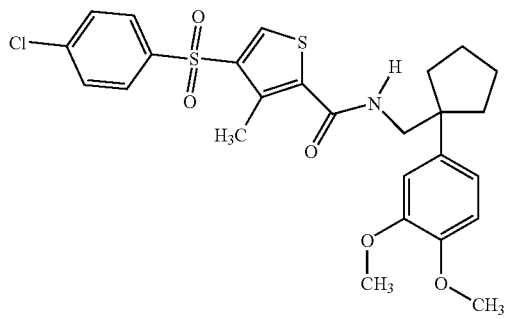 |

TABLE 1-continued
| Cmpd # | Compound |
|---|---|
| 72 | 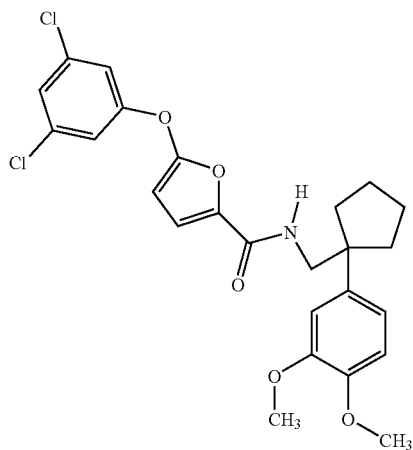 |
| 73 | 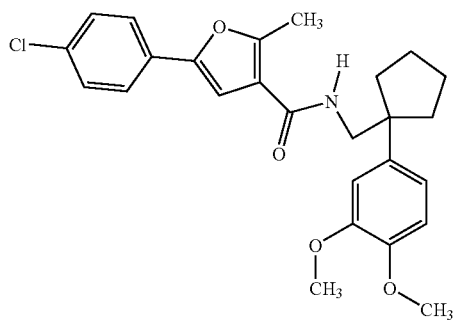 |
| 74 | 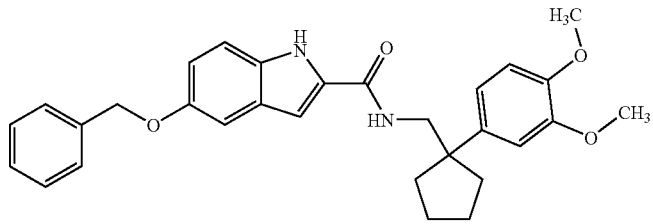 |
| 75 | 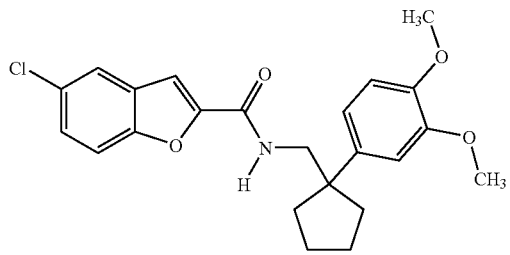 |

TABLE 1-continued
| Cmpd # | Compound |
|---|---|
| 76 | 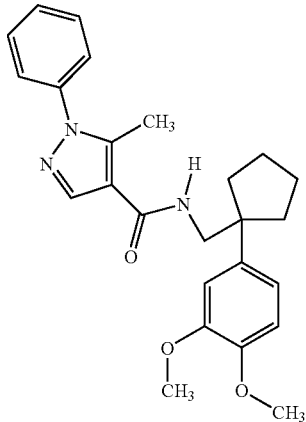 |
| 77 | 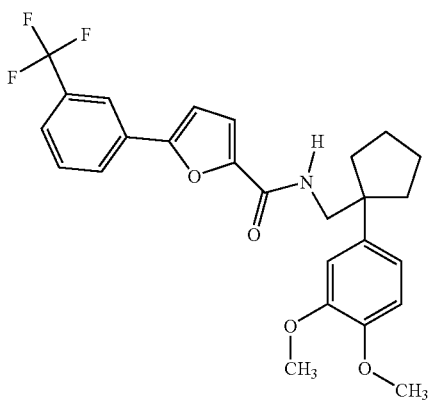 |
| 78 | 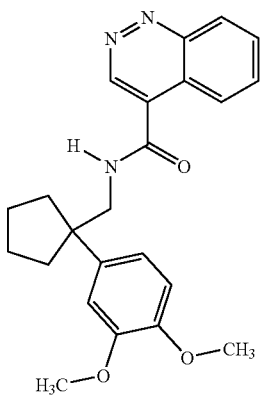 |

TABLE 1-continued
| Cmpd # | Compound |
|---|---|
| 79 | 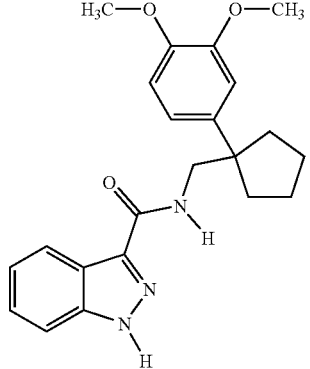 |
| 80 | 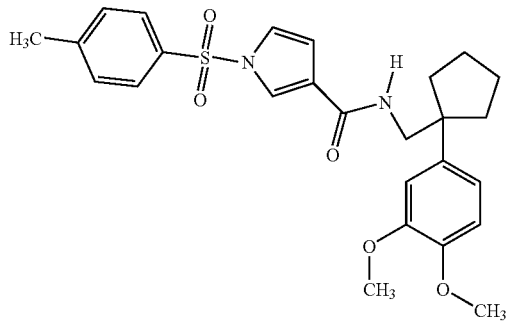 |
| 81 | 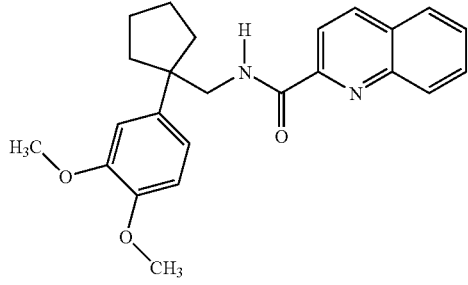 |
| 82 | 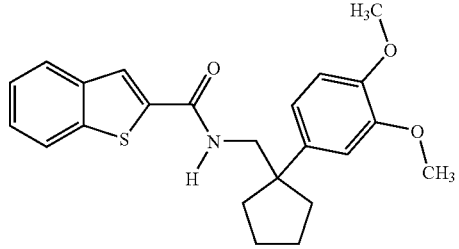 |

TABLE 1-continued
| Cmpd # | Compound |
|---|---|
| 83 | 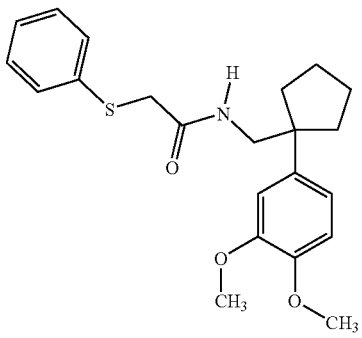 |
| 84 | 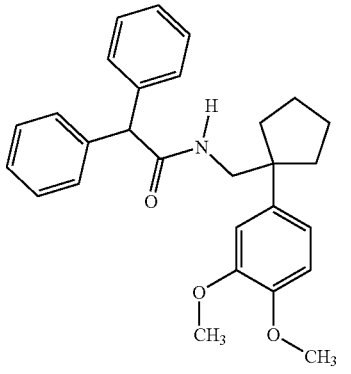 |
| 85 | 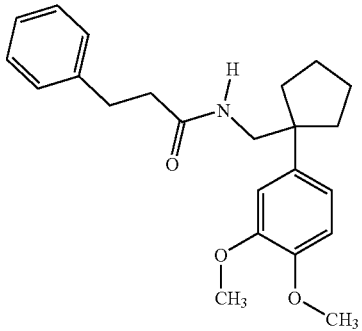 |
| 86 | 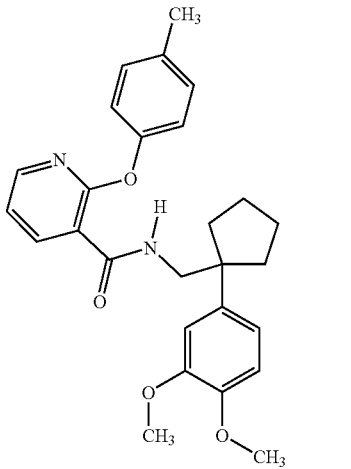 |

TABLE 1-continued
| Cmpd # | Compound |
|---|---|
| 87 | 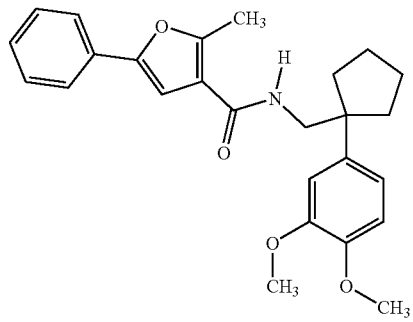 |
| 88 | 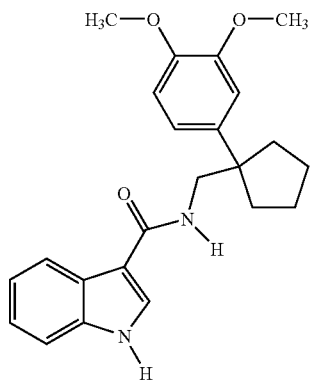 |
| 89 | 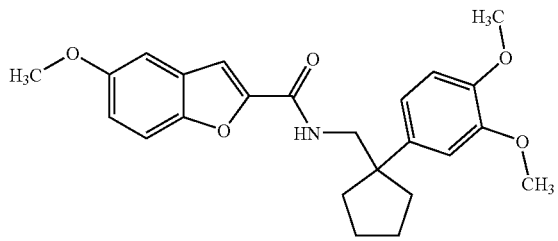 |
| 90 | 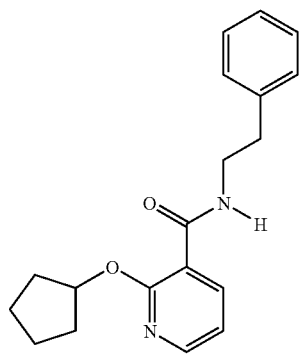 |

TABLE 1-continued
| Cmpd # | Compound |
|---|---|
| 91 | 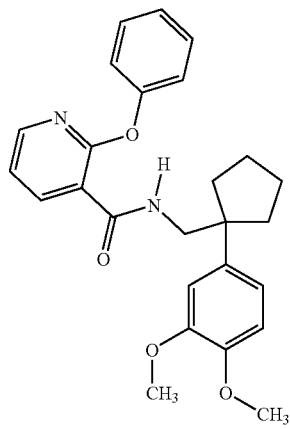 |
| 92 | 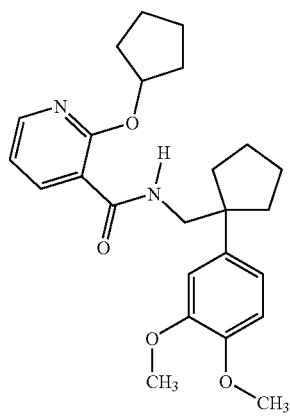 |
| 93 | 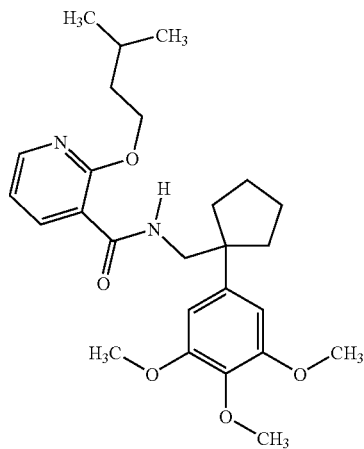 |

TABLE 1-continued
| Cmpd # | Compound |
|---|---|
| 94 | 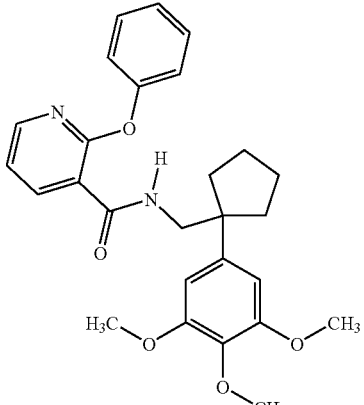 |
| 95 | 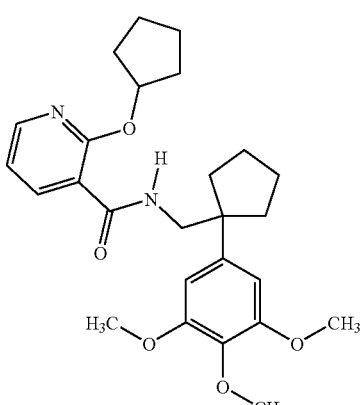 |
| 96 | 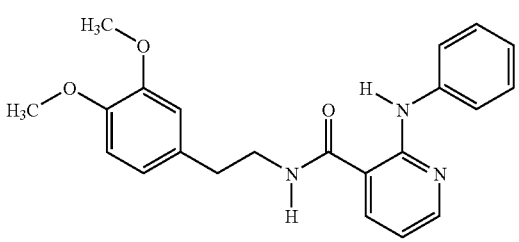 |
| 97 | 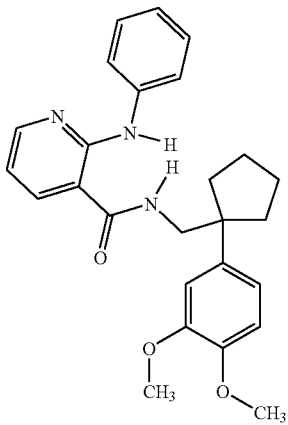 |

TABLE 1-continued
| Cmpd # | Compound |
|---|---|
| 98 | 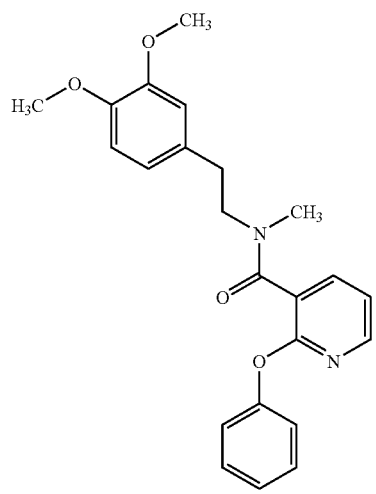 |
| 99 | 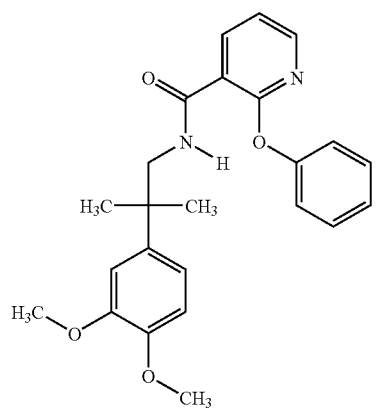 |
| 100 | 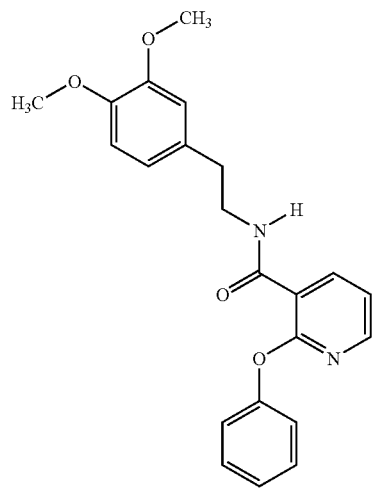 |

TABLE 1-continued
| Cmpd # | Compound |
|---|---|
| 101 | 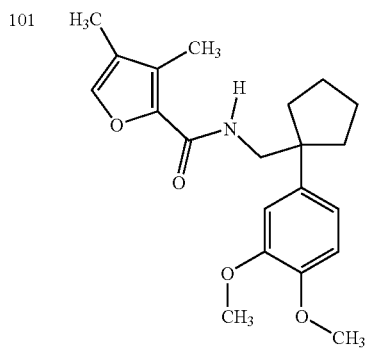 |
| 102 | 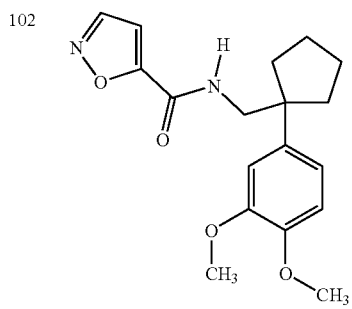 |
| 103 | 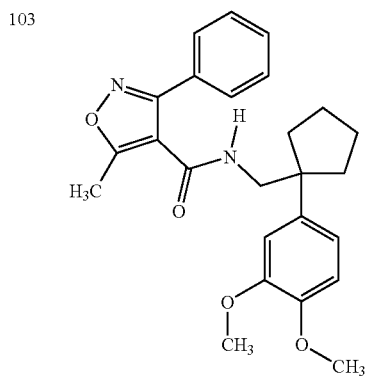 |
| 104 | 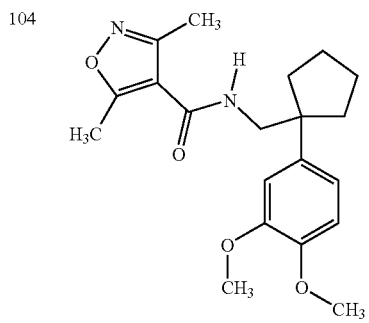 |

TABLE 1-continued
| Cmpd # | Compound |
| --- | --- |
| 105 | 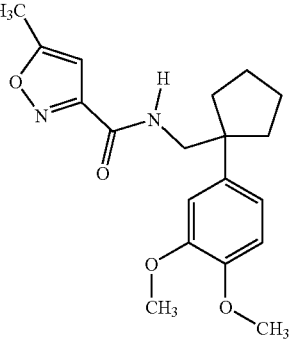 |
| 106 | 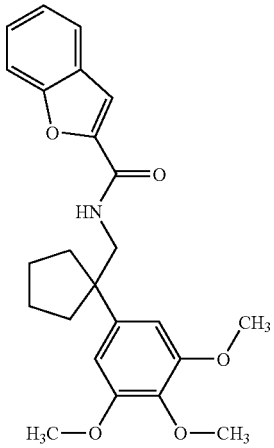 |
| 107 | 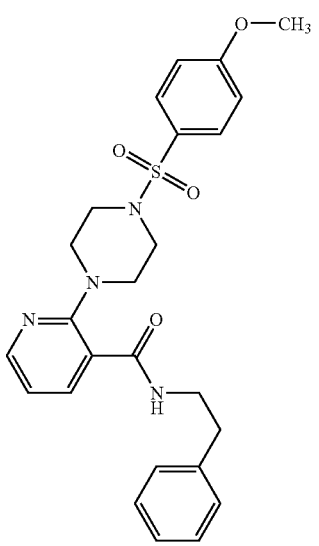 |

TABLE 1-continued

| Cmpd # | Compound |
|---|---|
| 108 | 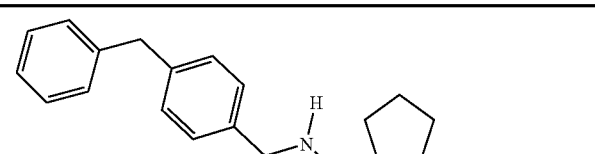 |

The compounds of the present invention can be prepared by methods well known in the art. An exemplary method of producing compounds of the present invention is shown below in Schemes 1-3.

Scheme 1 below illustrates an exemplary method for producing amine intermediates for compounds of the present invention wherein $R^C$ and $R^D$ cyclize to form a ring:

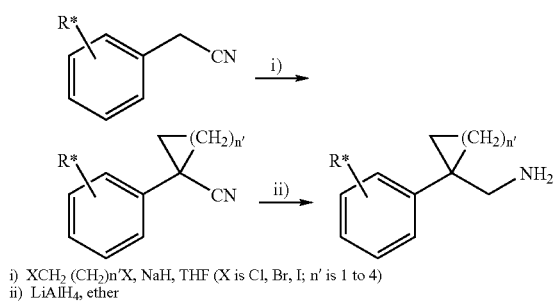

i) XCH$_2$(CH$_2$)n'X, NaH, THF (X is Cl, Br, I; n' is 1 to 4)
ii) LiAlH$_4$, ether An optionally substituted (R*) 2-phenylacetonitrile is reacted with an appropriate dihalo-alkyl compound, sodium hydride or the like, in THF or a similar solvent. The resulting spiro compound is reacted with lithium aluminum hydride or similar reducing reagent to provide the desired cyclic amine.

Scheme 2 below illustrates an exemplary method for producing amine intermediates for the present invention wherein $R^C$ and $R^D$ do not cyclize to form a ring.

Scheme 2:

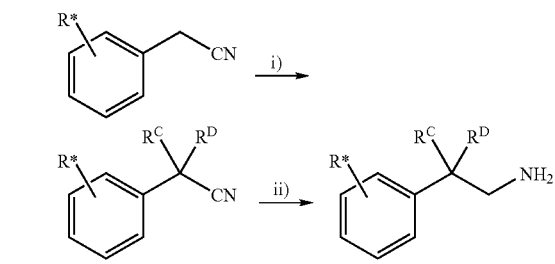

i) R$^C$H followed by R$^D$X, NaH, THF (X is Cl, Br, I)
ii) LiAlH$_4$, ether

Scheme 3 below illstrates an exemplary method for producing certain compounds of the present invention using the amine intermediates of, e.g., Scheme 1 and Scheme 2 above.

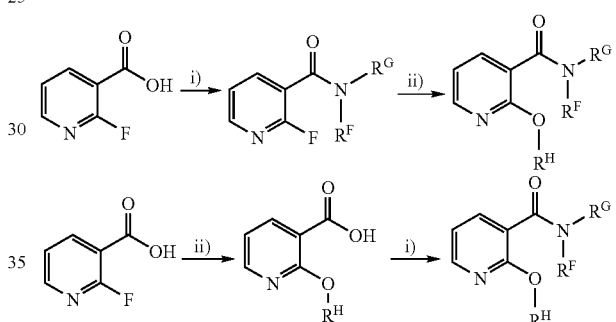

(i) Et$_3$N, CH$_3$CN or DMF, HATU, R$^F$R$^G$NH (amine intermediate from Scheme 1 or Scheme 2 above)
(ii) KHMDS, Toluene or DMF, R$^H$OH According to another preferred embodiment, the ABC transporter mediated disease is selected from Cystic fibrosis, COPD, Asthma, chronic pancreatitis, pneumonia, polycystic kidney disease, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma. The diseases associated with the latter class of ER malfunction are Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome.

Most preferably, the ABC transporter mediated disease is cystic fibrosis.

Another embodiment of the present invention provides a method of treating a disease selected from Cystic fibrosis, COPD, asthma, chronic pancreatitis, pneumonia, polycytic kidney disease, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, or Straussler-Scheinker syndrome comprising the step of administering to a mammal an effective amount of a composition comprising a compound according to the present invention.

According to a more preferred embodiment, the disease so treated is selected from Tangier's disease, stargardt disease 1, age related macular dystrophy 2, retinintis pigmentosa, bare lymphocyte syndrome, PFIC-3, anemia, progressive intrahepatic cholestasis-2, Dublin-Johnson syndrome, Pseudoxanthoma elasticum, cystic fibrosis, familial persistent hyperinsulinemic hyproglycemia of infancy, adrenolecukodystrophy, sitosterolemia, chronic obstructive pulmonary disease, asthma, disseminated bronchiectasis, chronic pancreatitis, male infertility, emphysema, or pneumonia.

According to another more preferred embodiment, the ABC transporter mediated disease is secretory diarrhea, COPD, or polycystic kidney disease in a mammal.

According to an alternative preferred embodiment, the present invention provides a method of treating cystic fibrosis or secretory diahrrea comprising the step of administering to said mammal a composition comprising the step of administering to said mammal a composition comprising a compound of the present invention, or a preferred embodiment thereof as set forth above. Most preferably, said disease is cystic fibrosis.

According to an alternative preferred embodiment, the present invention provides a method of modulating CFTR activity in a cell membrane ("potentiating") of a mammal in need thereof, comprising the step of administering to said mammal a composition comprising a compound of the present invention as defined above.

The preferred embodiments of the compounds of the present invention useful in potentiating the activity of CFTR include the preferred embodiments of the present invention described above.

According to an alternative embodiment, the present invention provides a method of increasing the number of functional ABC transporters in a membrane of a cell, comprising the step of contacting said cell with a compound of the present invention. The term "functional ABC transporter" as used herein means an ABC transporter that is capable of transport activity.

According to a preferred embodiment, said functional ABC transporter is CFTR.

The preferred embodiments of compounds of the present invention useful in increasing the number of functional ABC transporters include preferred embodiments of compounsd of the present invention as described above.

According to another embodiment, the present invention provides a method of modulating activity of an anion channel in vitro or in vivo, comprising the step of contacting said channel with a compound of the present invention. Preferably, said anion channel is a chloride channel or a bicarbonate channel. More preferably, said anion channel is a chloride channel.

According to yet another embodiment, the present invention provides a method of treating an anion channel mediated disease in a mammal, comprising the step of administering to said mammal a composition comprising a compound according to the present invention.

According to another embodiment, the present invention provides a pharmaceutical composition comprising:
(i) a compound of the present invention as described above;
(ii) a pharmaceutically acceptable carrier; and
(iii) an additional agent selected from a mucolytic agent, bronchodialator, an anti-biotic, an anti-infective agent, an anti-inflammatory agent, CFTR modulator other than a compound of the present invention, or a nutritional agent.

Preferred embodiments of compounds the present invention in the above pharmaceutical composition are those as described above.

According to another embodiment, the present invention provides a kit for use in measuring the activity of a ABC transporter or a fragment thereof in a biological sample in vitro or in vivo, comprising:
(i) a composition comprising a compound of the present invention; and
(ii) instructions for:
a) contacting the composition with the biological sample;
b) measuring activity of said ABC transporter or a fragment thereof.

According to a preferred embodiment, the kit is useful in measuring the activity of CFTR.

4. General Synthetic Methodology

The compounds of this invention may be prepared in general by methods known to those skilled in the art for analogous compounds, as illustrated by the general schemes below, and the preparative examples that follow. Starting materials are commercially available from typical chemical reagent supply companies, such as, Aldrich Chemicals Co., Sigma Chemical Company, ChemBridge Corporation, and the like. Compounds that are not commercially available can be prepared by those of ordinary skill in art following procedures set forth in references such as, "Fieser and Fieser's Reagents for Organic Synthesis", Volumes 1-15, John Wiley and Sons, 1991; "Rodd's Chemistry of Carbon Compounds", Volumes 1-5 and Supplementals, Elservier Science Publishers, 1989; and "Organic Reactions", Volumes 1-40, John Wiley and Sons, 1991.

Generally, the compounds of the present invention are prepared by the formation of an amide functionally between an optionally substituted carboxylic acid or acid chloride, and an optionally substituted primary amine.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

5. Uses, Formulation and Administration

Pharmaceutically Acceptable Compositions

As discussed above, the present invention provides compounds that are useful as modulators of ABC transporters and thus are useful in treating a disease selected from Cystic fibrosis, COPD, chronic pancreatitis, pneumonia, polycystic kidney disease, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, or Straussler-Scheinker syndrome comprising.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

6. Uses of Compounds and Pharmaceutically Acceptable Compositions

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of Formula I to a subject, preferably a mammal, in need thereof.

In certain preferred embodiments, the present invention provides a method of treating cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease, comprising the step of administering to said mammal an effective amount of a composition comprising a compound of Formula I, or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of the present invention.

According to the invention an "effective amount" of the compound or pharmaceutically acceptable composition is that amount effective for treating or lessening the severity of one or more of cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease.

The compounds and compositions, according to the method of the present invention, may be administered using any amount and any route of administration effective for treating or lessening the severity of one or more of cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of the present invention. In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of the present invention. The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" Biophys J 69 (4): 1272-80, and Gonzalez, J. E. and R. Y. Tsien (1997) "Improved indicators of cell membrane potential that use fluorescence resonance energy transfer" Chem Biol 4 (4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4 (9): 431-439).

These voltage sensitive assays are based on the change in fluorescence resonant energy transfer (FRET) between the membrane-soluble, voltage-sensitive dye, DiSBAC2 (3), and a fluorescent phospholipid, CC2-DMPE, which is attached to the outer leaflet of the plasma membrane and acts as a FRET donor. Changes in membrane potential (Vm) cause the negatively charged DiSBAC2 (3) to redistribute across the plasma membrane and the amount of energy transfer from CC2-DMPE changes accordingly. The changes in fluorescence emission can be monitored using VIPRTM II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of the present invention; and (ii) instructions for a) contacting the composition with the biological sample and b) measuring activity of said ABC transporter or a fragment thereof. In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of a composition of the present invention. In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

General Procedures

All reagents and solvents were used as received without further purification. Thin layer chromatography was performed on glass-backed silica gel 60 plates pre-coated with a fluorescent dye from EM Science. Mass spectrometry was performed in the positive mode on a PE SCIEX EX150 mass spectrometer. Purity was determined by the observed total ion current, and the ultraviolet absorption at 220 nm and 254 nm.

Example 1

Preparation of Certain Exemplary Amines

C-[1-(3,4-Dimethoxy-phenyl)-cyclopentyl]-methylamine (3,4-Dimethoxy-phenyl)-acetonitrile (5.00 g, 28.2 mmol) was dissolved in 60 mL of anhydrous tetrahydrofuran in a 250 mL round bottom flask. Sodium hydride (2.03 g, 84.6 mmol) was slowly added and the reaction mixture was warmed to 50-60° C. 1,4-Dichlorobutane (4.30 g, 33.9 mmol) was then added and the reaction mixture was heated to reflux for 16 hours. An additional aliquot of 1,4-dichlorobutane (4.30 g, 33.9 mmol) was added and the reaction mixture was refluxed for an additional 24 hours. The reaction mixture was cooled to room temperature and quenched with the slow addition of methanol. The reaction mixture was evaporated to dryness and purified by column chromatography on silica gel to yield a pale yellow oil (1.61 g, 6.98 mmol, 24.8%). The resulting 1-(3,4-dimethoxy-phenyl)-cyclopentanecarbonitrile (363 mg, 1.57 mmol) was dissolved in dry ether (4 mL) and cooled to 0° C. under an atmosphere of nitrogen. Lithium aluminum hydride (1.57 mL, 1M in ether) was slowly added and the reaction mixture was allowed to warm to room temperature and stirred for 16 hours. The reaction mixture was quenched with the slow addition of methanol. The reaction mixture was washed with a saturated aqueous sodium chloride solution, separated, and evaporated to dryness to give a colorless oil (356 mg, 1.38 mmol, 87.9%). ESI-MS m/z calc. 235.3, found 236.2 (M+1)$^+$. Retention time of 1.64 minutes.

[2-(3,4-Dimethoxy-phenyl)-2-methyl]-propylamine

Starting from 3,4-dimethoxyphenyl-acetonitrile (1 g, 5.64 mmol) and following a procedure similar to the one reported for the preparation of C-[1-(3,4-Dimethoxy-phenyl)-cyclopentyl]-methylamine, 250 mg (21% yield, 2 steps) of [2-(3,4-Dimethoxy-phenyl)-2-methyl]-propylamine were obtained as a colorless oil. ESI-MS m/z calc. 209.3, found 210 (M+1)$^+$. 1H NMR (400 MHz, CDCl3) δ 1.26 (s, 6H), 2.76 (s, 2H), 3.78 (s, 3H), 3.79 (s, 3H), 6.3-6.82 (m, 3H).

C-[1-(3,4-Dimethoxy-phenyl)-cyclohexyl]-methylamine (3,4-Dimethoxy-phenyl)-acetonitrile (5.00 g, 28.2 mmol) was dissolved in 60 mL of anhydrous tetrahydrofuran in a 250 mL round bottom flask. Sodium hydride (2.03 g, 84.6 mmol) was slowly added and the reaction mixture was warmed to 50-60° C. 1,4-Dichloropentane (4.78 g, 33.9 mmol) was then added and the reaction mixture was heated to reflux for 16 hours. The reaction mixture was cooled to room temperature and quenched with the slow addition of methanol. The reaction mixture was evaporated to dryness and purified by column chromatography on silica gel to yield a pale yellow oil (3.65 g, 14.9 mmol, 52.8%). The resulting 1-(3,4-dimethoxy-phenyl)-cyclohexanecarbonitrile (2.00 g, 8.15 mmol) was dissolved in dry ether (40 mL) and cooled to 0° C. under an atmosphere of nitrogen. Lithium aluminum hydride (8.15 mL, 1M in ether) was slowly added and the reaction mixture was allowed to warm to room temperature and stirred for 16 hours. The reaction mixture was cooled to 0° C. and quenched with 0.34 mL water, 0.34 mL of 15% sodium hydroxide, and then an additional 1.4 mL of water. The reaction mixture was then filtered through celite, washed with water and a saturated aqueous sodium chloride solution. The filtrate was evaporated to dryness to give a colorless oil (1.91 g, 7.66 mmol, 94.0%). ESI-MS m/z calc. 249.2, found 250.2 (M+1)$^+$. Retention time of 1.76 minutes.

Example 2

Preparation of Exemplary Compounds of Formula I

Benzofuran-2-carboxylic acid [1-(3,4-dimethoxy-phenyl)-cyclopentylmethyl]-amide

C-[1-(3,4-Dimethoxy-phenyl)-cyclopentyl]-methylamine (141 mg, 0.600 mmol) was dissolved in anhydrous 1,4-dioxane (2 mL) containing triethylamine (167 µL, 1.20 mmol). Benzofuran -2-carbonyl chloride (108 mg, 0.600 mmol) was then added and the reaction mixture was allowed to stir for 16 hours. The reaction mixture was filtered, evaporated to dryness, and purified by column chromatography on silica gel using a gradient of 5-50% ethyl acetate in hexanes. The pure fractions were combined and evaporated to dryness to yield a white solid (0.1775 g, 0.4678 mmol, 78.0%) ESI-MS m/z calc. 379.5, found 380.2 (M+1)$^+$. Retention time of 3.36 minutes. $^1$H NMR (400 MHz, DMSO-d6) δ 1.57-2.03 (m, 8H), 3.46 (d, J=6.4 Hz, 2H), 3.72 (s, 6H), 6.81-6.89 (m, 3H), 7.31 (t, J=7.5 Hz, 1H), 7.44 (t, J=7.8 Hz, 1H), 7.48 (s, 1H), 7.60 (d, J=8.4 Hz, 1H), 7.75 (d, J=8.4 Hz, 1H), 7.94 (t, J=6.3 Hz, 1H). $^{13}$C NMR (100 MHz, DMSO-d6) δ 23.1, 35.3, 47.2, 51.8, 55.5, 109.2, 111.5, 111.6, 111.7, 118.8, 122.6, 123.6, 126.7, 127.1, 139.3, 147.1, 148.3, 149.1, 154.1, 158.2.

Benzofuran-2-carboxylic acid [1-(3,4-dimethoxy-phenyl)-cyclohexylmethyl]-amide

C-[1-(3,4-Dimethoxy-phenyl)-cyclohexyl]-methylamine (276 mg, 1.12 mmol) and Benzofuran-2-carbonyl chloride (223 mg, 1.23 mmol) were dissolved in 6 mL of 1,4-dioxane containing triethylamine (312 µL, 2.24 mmol) at 0° C. The reaction mixture was evaporated to dryness, redissolved in dichloromethane, and extracted with 1M hydrochloric acid, 1M sodium hydroxide, and a saturated aqueous solution of sodium chloride. The organic layer dried over sodium sulfate and evaporated to dryness. The crude product was then purified by column chromatography on silica gel using a gradient of 0-20% ethyl acetate in hexanes. The pure fractions were combined and evaporated to dryness to yield a white solid (195 mg, 0.496 mmol, 44.2%). ESI-MS m/z calc. 393.2, found 394.2 (M+1)$^+$. Retention time of 2.96 minutes. $^1$H NMR (400 MHz, CD$_3$CN) δ 1.45-2.20 (m, 10H), 3.48 (d, J=6.5 Hz, 2H), 3.80 (s, 3H), 3.83 (s, 3H), 6.68 (s, 1H), 6.92-7.02 (m, 3H), 7.30-7.38 (m, 2H), 7.42-7.49 (m, 1H), 7.51-7.55 (m, 1H), 7.72 (d, J=7.8 Hz, 1H)

Quinoline-2-carboxylic acid [1-(3,4-dimethoxy-phenyl)-cyclopentylmethyl ]-amide

Quinoline-2-carboxylic acid (0.502 g, 2.90 mmol) and C-[1-(3,4-Dimethoxy-phenyl)-cyclopentyl]-methylamine (0.678 g, 2.90 mmol) were dissolved in acetonitrile (20 mL) containing triethylamine (894 µL, 6.38 mmol). O-(7-Azabenzotriazol-1-yl)-N,N,N',N'-tetramethyluronium hexafluorophosphate (1.54 g, 4.06 mmol) was added and the solution was allowed to stir for 16 hours. The reaction mixture was evaporated to dryness and purified by column chromatography on silica gel using a gradient of 0-40% ethyl acetate in hexanes. The pure fractions were combined and evaporated to dryness to yield a white solid (0.426 g, 1.09 mmol, 37.7%).

ESI-MS m/z calc. 390.2, found 391.2 (M+1)$^+$. Retention time of 3.94 minutes. $^1$H NMR (400 MHz, CD$_3$CN) δ 1.69-2.15 (m, 8H), 3.62 (d, J=30.1 Hz, 2H), 3.77 (s, 3H), 3.90 (s, 3H), 6.91-7.03 (m, 3H), 7.69 (t, J=8.1 Hz, 1H), 7.83 (t, J=7.7 Hz, 1H), 7.99 (t, J=8.8 Hz, 2H), 8.08 (s, 1H), 8.18 (d, J=8.5 Hz, 1H), 8.44 (d, J=8.5 Hz, 1H)

2-Fluoro-N-phenethyl-nicotinamide

2-Fluoro-nicotinic acid (0.793 g, 5.59 mmol) and phenethylamine (0.705 mL, 5.59 mmol) were dissolved in acetonitrile (20 mL) containing triethylamine (1.56 mL, 11.2 mmol). O-(7-Azabenzotriazol-1-yl)-N,N,N',N'-tetramethyluronium hexafluorophosphate (2.97 g, 7.83 mmol) was added and the solution was allowed to stir for 16 hours. The reaction mixture was evaporated to dryness and purified by column chromatography on silica gel using a gradient of 0-40% ethyl acetate in hexanes. The pure fractions were combined and evaporated to dryness to yield a white solid (0.196 g, 0.802 mmol, 14.3%). ESI-MS m/z calc. 244.1, found 245.2 (M+1)$^+$. Retention time of 2.76 minutes.

2-Butoxy-N-phenethyl-nicotinamide

2-Fluoro-N-phenethyl-nicotinamide (196 mg, 0.802 mmol), n-butanol (700 µL, 7.65 mmol) and potassium bis (trimethylsilyl)amide (2.5 mL, 0.5 M in toluene) were combined and stirred for 5 minutes at room temperature. The reaction mixture was evaporated to dryness and purified by column chromatography on silica gel using a gradient of 0-20% ethyl acetate in hexanes. The pure fractions were combined and evaporated to dryness to yield a colorless oil (207 mg, 0.694 mmol, 86.5%). ESI-MS m/z calc. 298.2, found 299.2 (M+1)$^+$. Retention time of 3.46 minutes. H NMR (400 MHz, CD$_3$CN) δ, 0.95 (t, J=7.4 Hz, 3H), 1.34-1.44 (m, 2H), 1.63-1.70 (m, 2H), 2.91 (t, J=7.0 Hz, 2H), 3.65-3.73 (m, 2H), 4.41 (t, J=6.7 Hz, 2H), 7.08 (dd, J=7.5, 4.8 Hz, 1H), 7.23-7.37 (m, 5H), 8.01 (s, 1H), 8.25 (dd, J=4.8, 2.0 Hz, 1H), 8.39 (dd, J=7.5, 2.0 Hz, 1H).

Benzofuran-2-carboxylic acid [2-(3,4-dimethoxy-phenyl)-2-methyl-propyl]-amide 2-(3,4-Dimethoxy-phenyl)-2-methyl-propylamine (106 mg, 0.506 mmol) and benzofuran-2-carbonyl chloride (90.7 mg, 0.502 mmol) were dissolved in 2 mL of 1,4-dioxane containing triethylamine (139 µL, 1.00 mmol). The reaction mixture was stirred for 15 hours, evaporated to dryness, redissolved in dichloromethane, and extracted with 1M hydrochloric acid, 1M sodium hydroxide, and a saturated aqueous solution of sodium chloride. The organic layer dried over sodium sulfate and evaporated to dryness. The crude product was then purified by column chromatography on silica gel using a gradient of 1-30% ethyl acetate in hexanes. The pure fractions were combined and evaporated to dryness to yield a white solid (153 mg, 0.433 mmol, 86.3%). ESI-MS m/z calc. 353.2, found 354.2 (M+1)$^+$. Retention time of 2.99 minutes. $^1$H NMR (400 MHz, CD$_3$CN) δ 1.38 (s, 6H), 3.60 (s, 2H), 3.81 (s, 3H), 3.83 (s, 3H), 6.85-7.06 (m, 4H), 7.31-7.39 (m, 2H), 7.46 (t, J=8.4 Hz, 1H), 7.52-7.56 (m, 1H), 7.72 (d, J=8.2 Hz, 1H).

Benzofuran-2-carboxylic acid [1-(3,4,5-trimethoxy-phenyl)-cyclopentylmethyl]-amide C-[1-(3,4,5-Trimethoxy-phenyl)-cyclopentyl]-methylamine (53.1 mg, 0.200 mmol) and benzofuran-2-carbonyl chloride (36.1 mg, 0.200 mmol) were dissolved in 2 mL of 1,4-dioxane containing triethylamine (84 μL, 0.60 mmol). The reaction mixture was stirred for 15 hours, evaporated to dryness, and purified by reverse phase preparative liquid chromatography to yield the pure product (9.59 mg, 0.0234 mmol, 11.7%). ESI-MS m/z calc. 409.2, found 410.4 (M+1)$^+$. Retention time of 3.29 minutes.

Benzofuran-2-carboxylic acid (1-benzo[1,3]dioxol-5-yl-cyclopentylmethyl)-amide

C-(1-Benzo[1,3]dioxol-5-yl-cyclopentyl)-methylamine (43.8 mg, 0.200 mmol) and benzofuran-2-carbonyl chloride (36.1 mg, 0.200 mmol) were dissolved in 2 mL of 1,4-dioxane containing triethylamine (83.6 μL, 0.600 mmol). The reaction mixture was stirred for 15 hours, evaporated to dryness, and purified by reverse phase preparative liquid chromatography to yield the pure product (13.0 mg, 0.0358 mmol, 17.8%). ESI-MS m/z calc. 363.2, found 364.2 (M+1)$^+$. Retention time of 4.22 minutes.

2-Cyclopentyloxy-N-phenethyl-nicotinamide

2-Fluoro-nicotinic acid (84.7 mg, 0.600 mmol, cyclopentanol (51.6 mg, 0.600 mmol) and potassium bis(trimethylsilyl)amide (478 mg, 2.40 mmol) were combined in 0.6 mL of N,N-dimethylformamide and subjected to microwave irradiation for 3 minutes at 180° C. Phenethylamine (72.7 mg, 0.600 mmol) and O-(7-azabenzotriazol-1-yl)-N,N,N',N'-tetramethyluronium hexafluorophosphate (304 mg, 0.800 mmol) was added and the solution was allowed to stir for 16 hours. The mixture was then purified by reverse phase preparative liquid chromatography to yield the pure product (2.9 mg, 0.0093 mmol, 1.6%) ESI-MS m/z calc. 310.2, found 311.2 (M+1)$^+$. Retention time of 3.40 minutes.

N-[2-(3,4-Dimethoxy-phenyl)-ethyl]-N-methyl-2-(3-methyl-butoxy)-nicotinamide

2-Fluoro-nicotinic acid (84.7 mg, 0.600 mmol, 3-methyl-butan-1-ol (52.9 mg, 0.600 mmol) and potassium bis(trimethylsilyl)amide (478 mg, 2.40 mmol) were combined in 0.6 mL of N,N-dimethylformamide and subjected to microwave irradiation for 3 minutes at 180° C. [2-(3,4-Dimethoxy-phenyl)-ethyl]-methyl-amine (117 mg, 0.600 mmol) and O-(7-azabenzotriazol-1-yl)-N,N,N',N'-tetramethyluronium hexafluorophosphate (304 mg, 0.800 mmol) was added and the solution was allowed to stir for 16 hours. The mixture was then purified by reverse phase preparative liquid chromatography to yield the pure product (1.5 mg, 0.0039 mmol, 0.65%) ESI-MS m/z calc. 386.2, found 387.4 (M+1)$^+$. Retention time of 2.98 minutes.

1H-Indazole-3-carboxylic acid [1-(3,4-dimethoxy-phenyl)-cyclopentylmethyl]-amide 1H-Indazole-3-carboxylic acid (32.4 mg, 0.200 mmol) and C-[1-(3,4-Dimethoxy-phenyl)-cyclopentyl]-methylamine (47.1 g, 0.200 mmol) were dissolved in acetonitrile (1 mL) containing triethylamine (83.6 μL, 0.600 mmol). O-(7-Azabenzotriazol-1-yl)-N,N,N',N'-tetramethyluronium hexafluorophosphate (76.0 mg, 0.200 mmol) was added and the solution was allowed to stir for 16 hours. The mixture was then purified by reverse phase preparative liquid chromatography to yield the pure product (7.47 mg, 0.0197 mmol, 9.84%) ESI-MS m/z calc. 379.2, found 380.4 (M+1)$^+$. Retention time of 3.02 minutes.

4-Benzyl-N-[1-(3,4-dimethoxy-phenyl)-cyclopentylmethyl]-benzamide

4-Benzyl-benzoic acid (21.2 mg, 0.100 mmol) and C-[1-(3,4-Dimethoxy-phenyl)-cyclopentyl]-methylamine (23.5 g, 0.100 mmol) were dissolved in acetonitrile (1 mL) containing triethylamine (41.8 μL, 0.300 mmol). O-(7-Azabenzotriazol-1-yl)-N,N,N',N'-tetramethyluronium hexafluorophosphate (38.0 mg, 0.100 mmol) was added and the solution was allowed to stir for 16 hours. The mixture was then purified by reverse phase preparative liquid chromatography to yield the pure product (24.1 mg, 0.0561 mmol, 56.1%) ESI-MS m/z calc. 429.2, found 430.4 (M+1)$^+$. Retention time of 3.75 minutes.

N-[1-(3,4-Dimethoxy-phenyl)-cyclopentylmethyl]-2,2-diphenyl-acetamide

Diphenyl-acetic acid (42.4 mg, 0.200 mmol) and C-[1-(3,4-Dimethoxy-phenyl)-cyclopentyl]-methylamine (47.1 g, 0.200 mmol) were dissolved in acetonitrile (1 mL) containing triethylamine (83.6 μL, 0.600 mmol). O-(7-Azabenzotriazol-1-yl)-N,N,N',N'-tetramethyluronium hexafluorophosphate (76.0 mg, 0.200 mmol) was added and the solution was allowed to stir for 16 hours. The mixture was then purified by reverse phase preparative liquid chromatography to yield the pure product (13.3 mg, 0.0310 mmol, 15.5%) ESI-MS m/z calc. 429.2, found 430.2 (M+1)$^+$. Retention time of 3.47 minutes.

2-Methyl-5-phenyl-furan-3-carboxylic acid [1-(3,4-dimethoxy-phenyl)-cyclopentylmethyl]-amide 2-Methyl-5-phenyl-furan-3-carboxylic acid (40.4 mg, 0.200 mmol) and C-[1-(3,4-Dimethoxy-phenyl)-cyclopentyl]-methylamine (47.1 g, 0.200 mmol) were dissolved in acetonitrile (1 mL) containing triethylamine (83.6 μL, 0.600 mmol). O-(7-Azabenzotriazol-1-yl)-N,N,N',N'-tetramethyluronium hexafluorophosphate (76.0 mg, 0.200 mmol) was added and the solution was allowed to stir for 16 hours. The mixture was then purified by reverse phase preparative liquid chromatography to yield the pure product (17.0 mg, 0.0405 mmol, 20.3%) ESI-MS m/z calc. 419.2, found 420.4 (M+1)$^+$. Retention time of 3.62 minutes.

N-[1-(3,4-Dimethoxy-phenyl)-cyclopentylmethyl]-2-phenylsulfanyl-acetamide

Phenylsulfanyl-acetic acid (33.6 mg, 0.200 mmol) and C-[1-(3,4-Dimethoxy-phenyl)-cyclopentyl]-methylamine (47.1 g, 0.200 mmol) were dissolved in acetonitrile (1 mL) containing triethylamine (83.6 μL, 0.600 mmol). O-(7-Azabenzotriazol-1-yl)-N,N,N',N'-tetramethyluronium hexafluorophosphate (76.0 mg, 0.200 mmol) was added and the solution was allowed to stir for 16 hours. The mixture was then purified by reverse phase preparative liquid chromatography to yield the pure product (11.3 mg, 0.0293 mmol, 14.6%) ESI-MS m/z calc. 385.2, found 386.0 (M+1)$^+$. Retention time of 3.12 minutes.

N-[1-(3,4-Dimethoxy-phenyl)-cyclopentylmethyl]-3-phenyl-propionamide

3-Phenyl-propionic acid (30.0 mg, 0.200 mmol) and C-[1-(3,4-Dimethoxy-phenyl)-cyclopentyl]-methylamine (47.1 g, 0.200 mmol) were dissolved in acetonitrile (1 mL) containing triethylamine (83.6 μL, 0.600 mmol). O-(7-Azabenzotriazol- 1-yl)-N,N,N',N'-tetramethyluronium hexafluorophosphate (76.0 mg, 0.200 mmol) was added and the solution was allowed to stir for 16 hours. The mixture was then purified by reverse phase preparative liquid chromatography to yield the pure product (19.0 mg, 0.0517 mmol, 25.8%) ESI-MS m/z calc. 367.2, found 367.5 (M+1)$^+$. Retention time of 3.05 minutes.

The characterization data for certain compounds of the present invention are shown below in Table 2.

TABLE 2

| Cmpd # | LC-MS ((M + 1)$^+$) | LC-RT (min) |
|---|---|---|
| 7 | 379.50 | 3.90 |
| 17 | 319.20 | 3.03 |
| 27 | 394.20 | 2.96 |
| 34 | 354.20 | 3.70 |
| 35 | 364.20 | 4.22 |
| 36 | 359.20 | 2.51 |
| 37 | 345.00 | 2.80 |
| 38 | 317.20 | 2.36 |
| 39 | 345.20 | 2.81 |
| 40 | 243.20 | 3.17 |
| 41 | 371.20 | 2.81 |
| 42 | 373.40 | 2.64 |
| 43 | 373.20 | 3.22 |
| 44 | 331.40 | 2.60 |
| 45 | 299.20 | 3.40 |
| 46 | 359.00 | 3.00 |
| 47 | 387.40 | 3.03 |
| 48 | 359.00 | 3.03 |
| 49 | 257.00 | 2.65 |
| 50 | 271.20 | 2.93 |
| 51 | 299.20 | 3.38 |
| 52 | 313.00 | 3.60 |
| 53 | 285.00 | 3.17 |
| 54 | 359.20 | 2.55 |
| 55 | 373.20 | 2.83 |
| 56 | 385.40 | 2.86 |
| 57 | 331.40 | 2.13 |
| 58 | 345.20 | 2.40 |
| 59 | 398.40 | 2.81 |
| 60 | 414.40 | 3.00 |
| 61 | 412.20 | 2.76 |
| 62 | 428.40 | 2.93 |
| 63 | 338.00 | 3.07 |
| 64 | 354.20 | 3.25 |
| 65 | 452.20 | 3.37 |
| 66 | 468.20 | 3.57 |
| 67 | 391.20 | 3.27 |
| 68 | 393.20 | 3.42 |
| 69 | 391.00 | 2.50 |
| 70 | 391.00 | 2.24 |
| 71 | 534.40 | 3.57 |
| 72 | 490.20 | 3.87 |
| 73 | 454.40 | 3.90 |
| 74 | 485.40 | 3.63 |
| 75 | 414.40 | 3.53 |
| 76 | 420.00 | 3.02 |
| 77 | 474.40 | 3.70 |
| 78 | 392.00 | 2.58 |
| 79 | 380.40 | 3.02 |
| 80 | 483.20 | 3.35 |
| 81 | 391.00 | 3.45 |
| 82 | 396.20 | 3.38 |
| 83 | 386.00 | 3.12 |
| 84 | 430.20 | 3.47 |
| 85 | 368.20 | 3.05 |
| 86 | 447.40 | 3.45 |
| 87 | 420.40 | 3.62 |
| 88 | 379.40 | 2.83 |
| 89 | 410.40 | 3.25 |
| 90 | 311.20 | 3.40 |
| 91 | 433.40 | 3.27 |
| 92 | 425.40 | 3.60 |
| 93 | 457.40 | 3.72 |
| 94 | 463.40 | 3.23 |

TABLE 2-continued

| Cmpd # | LC-MS ((M + 1)$^+$) | LC-RT (min) |
|---|---|---|
| 95 | 455.40 | 3.53 |
| 96 | 378.40 | 2.23 |
| 97 | 432.60 | 2.83 |
| 98 | 393.40 | 2.60 |
| 99 | 407.40 | 2.95 |
| 100 | 379.40 | 2.68 |
| 101 | 358.20 | 3.05 |
| 102 | 331.40 | 2.65 |
| 103 | 421.20 | 3.20 |
| 104 | 359.20 | 2.70 |
| 105 | 345.00 | 2.91 |
| 106 | 410.40 | 3.29 |
| 107 | 481.20 | 2.75 |
| 108 | 430.40 | 3.75 |

Example 3

Preparation of Additional Compounds of Formula I

Following the procedures taught in the specification and the preceding Examples, the following compounds of Formula I can be prepared.

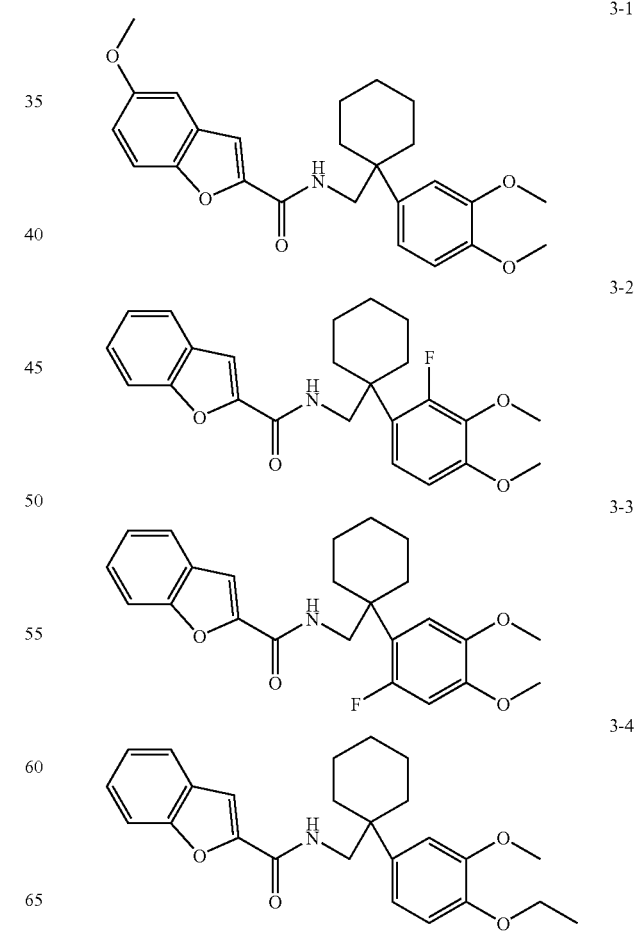

-continued

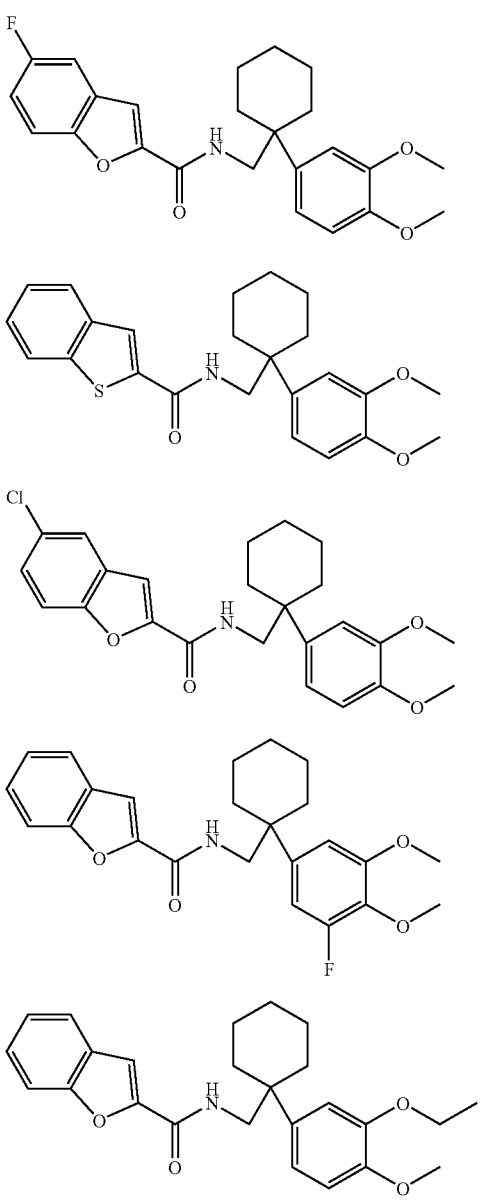

3-1: 5-methoxy-N-((1-(3,4-dimethoxyphenyl)-cyclohexyl) methyl)benzofuran-2-carboxamide
3-2: N-((1-(2-fluoro-3,4-dimethoxyphenyl)cyclohexyl)methyl)-benzofuran-2-carboxamide
3-3: N-((1-(2-fluoro-4,5-dimethoxyphenyl)cyclohexyl)methyl)-benzofuran-2-carboxamide
3-4: N-((1-(4-ethoxy-3-methoxyphenyl)cyclohexyl)methyl)-benzofuran-2-carboxamide
3-5: 5-fluoro-N-((1-(3,4-dimethoxyphenyl)cyclohexyl)-methyl)benzofuran-2-carboxamide
3-6: N-((1-(3,4-dimethoxyphenyl)cyclohexyl)-methyl) benzo[b]thiophene-2-carboxamide
3-7: 5-chloro-N-((1-(3,4-dimethoxyphenyl)cyclohexyl)methyl)-benzofuran-2-carboxamide
3-8: N-((1-(3-fluoro-4,5-dimethoxyphenyl)cyclohexyl)methyl)-benzofuran-2-carboxamide
3-9: N-((1-(3-ethoxy-4-methoxyphenyl)cyclohexyl)methyl)-benzofuran-2-carboxamide Example 4

Assays for Detecting and Measuring ΔF508-CFTR Correction Properties of Compounds Membrane Potential Optical Methods for Assaying ΔF508-CFTR Modulation Properties of Compounds.

The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" Biophys J 69 (4): 1272-80, and Gonzalez, J. E. and R. Y. Tsien (1997) "Improved indicators of cell membrane potential that use fluorescence resonance energy transfer" Chem Biol 4 (4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4 (9): 431-439).

These voltage sensitive assays are based on the change in fluorescence resonant energy transfer (FRET) between the membrane-soluble, voltage-sensitive dye, DiSBAC$_2$ (3), and a fluorescent phospholipid, CC2-DMPE, which is attached to the outer leaflet of the plasma membrane and acts as a FRET donor. Changes in membrane potential ($V_m$) cause the negatively charged DiSBAC$_2$ (3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 µM forskolin and the CFTR potentiator, genistein (20 µM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

Identification of Potentiator Compounds

To identify potentiators of ΔF508-CFTR; a double-addition HTS assay format was developed. During the first addition, a Cl⁻ free medium with or without test compound was added to each well. After 22 sec, a second addition of Cl⁻-free medium containing 2-10 µM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

| Solutions | |
|---|---|
| Bath Solution #1: (in mM) | NaCl 160, KCl 4.5, CaCl$_2$ 2, MgCl$_2$ 1, HEPES 10, pH 7.4 with NaOH. |
| Chloride-free bath solution: | Chloride salts in Bath Solution #1 are substituted with gluconate salts. |
| CC2-DMPE: | Prepared as a 10 mM stock solution in DMSO and stored at −20° C. |
| DiSBAC$_2$(3): | Prepared as a 10 mM stock in DMSO and stored at −20° C. |

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours).

Electrophysiological Assays for Assaying ΔF508-CFTR Modulation Properties of Compounds 1. Ussing Chamber Assay Ussing chamber experiments were performed on polarized epithelial cells expressing ΔF508-CFTR to further characterize the ΔF508-CFTR modulators identified in the optical assays. FRT$^{\Delta F508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl$^-$ through ΔF508-CFTR expressed in the apical membrane. The I$_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane Cl$^-$ concentration gradient. To set up this gradient, normal ringer was used on the basolateral membrane, whereas apical NaCl was replaced by equimolar sodium gluconate (titrated to pH 7.4 with NaOH) to give a large Cl$^-$ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 370C and were subsequently washed 3× prior to recording. The cAMP- and genistein-mediated I$_{SC}$ in compound-treated cells was normalized to the 27° C. and 37° C. controls and expressed as percentage activity. Preincubation of the cells with the correction compound significantly increased the cAMP- and genistein-mediated I$_{SC}$ compared to the 37° C. controls.

Identification of Potentiator Compounds

Typical protocol utilized a basolateral to apical membrane Cl$^-$ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl$^-$ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

Solutions

Basolateral solution (in mM): NaCl (135), CaCl$_2$ (1.2), MgCl$_2$ (1.2), K$_2$HPO$_4$ (2.4), KHPO$_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

Cell Culture

Fisher rat epithelial (FRT) cells expressing ΔF508-CFTR (FRT$^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% CO$_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

2. Whole-cell Recordings

The macroscopic ΔF508-CFTR current (I$_{\Delta F508}$) in temperature- and test compound-corrected NIH3T3 cells stably expressing ΔF508-CFTR were monitored using the perforated-patch, whole-cell recording. Briefly, voltage-clamp recordings of I$_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl$^-$ (EC$_1$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Solutions

Intracellular solution (in mM): Cs-aspartate (90), CsCl (50), $MgCl_2$ (1), HEPES (10), and 240 µg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), HEPES (10) (pH adjusted to 7.35 with HCl).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1× NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≦ 2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Compounds of the invention demonstrated activity as modulators of ATP binding cassette transporters, specifically CFTR.

Example 5 cAMP Measurements of Certain Compounds

This example shows that certain compounds with similar structures have varying effects on cAMP (adenosine 3, 5-cyclic monophosphate) levels. ABC Transfer proteins, and CFTR in particular are cAMP regulated ion channels. Ideally, a modulator compound of such a protein should not cause a change in cAMP levels.

In the following example, the effect on cAMP levels by three structurally similar compounds from Table 1 were determined using the cAMP levels from 20 µM forskolin as the normalized reference measure.

Tropix® Assay for Measurement of cAMP

The level of cAMP in FRT cells following 0.5 µM forskolin or test compound application was determined using a commercially available chemiluminiscent immunoassay system for mammalian cells called Tropix® (Applied Biosystems, Bedford, Mass.). Briefly, FRT cells were incubated for 15 minutes with a test compound in the presence and absence of 0.5 µM forskolin. The compounds were aspirated and the cells were then lysed and transferred along with the lysis buffer to a 96-well Tropix® ELISA plate. A cAMP-Alk Phos conjugate is then added to the assay plate, followed by the addition of cAMP anti-body. After several wash and aspiration steps, Sapphire blue II solution is added and the fluorescence emission is read on the Topcount fluorescence reader, and the cAMP concentrations were determined using a cAMP standard curve that was present in each plate.

Results

The compound N-((1-(3,4-dimethoxyphenyl)-cyclopentyl)methyl)benzofuran-2-carboxamide, (Table 1, Compound 7) has previously been reported in the literature as a potentiator of ΔF508-CFTR (J Biol Chem; 277 (40): 37235-41, 2002). The authors have shown that the mechanism of this activation was via the rise in cellular cAMP. This compound was shown to increase cAMP content alone and also potentiated the cAMP elevation educed by the low concentration (0.5 µM) of forskolin, similar to that found for 20 µM forskolin. We were able to produce similar results in our Tropix® system. Compound 7 alone, generated an average of 40.3±3.5% of cAMP produced by 20 µM of forskolin, which was a significant increase compared with the DMSO control, 24.8±3.9% of 20 µM forskolin, n=4, p<0.05. In the presence of 0.5 µM forskolin, compound 7 generated an average of 92.3±2.7% of cAMP produced by 20 µM of forskolin, which was also a significant increase compared with the 0.5 µM forskolin control, 45.9±3.0% of 20 µM forskolin, n=4, p<0.05.

It has been surprisingly found that compounds with similar structures show statistically significant varying levels of activities in this cAMP assay. For example, the compound N-(2-(3,4-dimethoxyphenyl)-2-methylpropyl)benzofuran-2-carboxamide (Table 1, Compound 34) alone, generated an average of 24.4±1.1% of cAMP produced by 20 µM of forskolin, which was not a significant increase compared with the DMSO control 24.8±3.9% of 20 µM forskolin, n=4. But in the presence of 0.5 µm forskolin, Compound 34 generated an average of 61.5±1.8% of cAMP produced by 20 µM of forskolin, which was a significant increase compared with the 0.5 µM forskolin control, 45.9±3.0% of 20 µM forskolin, n=4, p<0.05.

In comparison, the compound N-((1-(3,4-dimethoxyphenyl)cyclohexyl)methyl)benzofuran-2-carboxamide, Table 1, Compound 25, by itself generated an average of 7.9±1.1% of cAMP produced by 20 µM of forskolin, which was not a significant increase compared with the DMSO control of 8.4±2.8% of 20 µm forskolin, n=4. Surprisingly, Compound 25 in the presence of 0.5 µM forskolin generated an average of 27.1±1.8% of cAMP produced by 20 µM of forskolin, which was also not a significant increase compared with the 0.5 µM forskolin control, 32.2±3.2% of 20 µM forskolin, n=4.

The example teaches that compounds can have potentiator activity without having an accompanying increase in cAMP concentrations.

The invention claimed is:

1. A compound of formula II:

$$R^{B(n)} - \phantom{x} \begin{array}{c} R^C \; R^D \\ \phantom{x} \end{array} - \text{CH}_2 - \text{N(H)} - A - Z$$

II or a pharmaceutically acceptable salt thereof, wherein:
A is C(O) or $SO_2$;
$R^C$ and $R^D$ taken together form a 3-6 membered cycloalkyl ring;
n is 2 or 3;
Z is

[structure with W ring and $R^{Z(m)}$]

wherein,
W is pyridyl, pyrazolyl, oxazazolyl, furanyl, thienyl, isoxazolyl, pyrrolyl, benzofuranyl, benzothienyl, indolyl, indazolyl, quinolinyl, isoquinolinyl or cinnolinyl and m is 0 to 5;
$R^B$ is (C1-C4)alkoxy;
$R^Z$ is independently selected from $R^1$, $R^2$, $R^4$, or $R^5$, wherein:
$R^1$ is $R^6$, ((C1-C4)aliphatic)-Y, or Y; and
Y is halo, CN, $NO_2$, $CF_3$, $OCF_3$, OH, $SR^6$, $S(O)R^6$, $SO_2R^6$, $NH_2$, $NHR^6$, $N(R^6)_2$, COOH, $COOR^6$ or $OR^6$;
$R^2$ is an aliphatic, wherein each $R^2$ comprises up to 2 substituents independently selected from $R^4$, or $R^5$;
$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^5C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^5SO_2R^6$, $NR^6SO_2N(R^6)_2$, $NR^5SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;
$R^5$ is a cycloaliphatic, aryl, heterocyclic, or heteroaryl ring, wherein each $R^5$ is optionally substituted with up to 3 $R^1$ substituents; and
$R^6$ is H or aliphatic, provided that when A is C(O), then the following compounds are excluded:

| $R^C$ & $R^D$ together | ring W together with $R^Z$ and m | ring B with $R^B$ & n |
|---|---|---|
| cyclopentyl | benzofuran-2-yl | 3,4-dimethoxyphenyl |
| cyclohexyl | benzofuran-2-yl | 3,4-dimethoxyphenyl |

-continued

| $R^C$ & $R^D$ together | ring W together with $R^Z$ and m | ring B with $R^B$ & n |
|---|---|---|
| cyclopentyl | diphenylmethyl | 3,4-dimethoxyphenyl |
| cyclopentyl | 5-bromo-furan-2-yl | 3,4-dimethoxyphenyl. |

2. The compound according to claim 1, wherein $R^C$ and $R^D$, taken together, form a 5-membered cycloalkyl ring.

3. The compound according to claim 1, wherein $R^C$ and $R^D$, taken together, form a 6-membered cycloalkyl ring.

4. The compound according to claim 1, wherein W is an indolyl, benzofuranyl, benzothienyl, pyrazolyl or indazolyl.

5. The compound according to claim 4, wherein W is an indol-2-yl, indol-3-yl, benzofuran-2-yl, benzothien-2-yl, pyrazol-3-yl, pyrazol-4-yl or indazol-3-yl.

6. The compound according to claim 1, wherein W is a furanyl, thienyl, isoxazolyl, or pyrrolyl.

7. The compound according to claim 1, wherein W is a quinolinyl or cinnolinyl.

8. The compound of claim 1 wherein W is a benzofuranyl, indolyl, pyrazolyl, oxazazolyl, furanyl, quinolinyl, isoquinolinyl or cinnolinyl.

9. The compound of claim 1 wherein $R^C$ and $R^D$ taken together form cyclohexyl.

10. The compound of claim 1 wherein n is 2.

11. The compound of claim 10 wherein $R^B$ is methoxy.

12. The compound of claim 1 wherein n is 3.

13. The compound of claim 1, wherein the compound is selected from

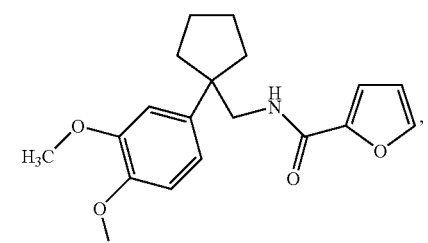

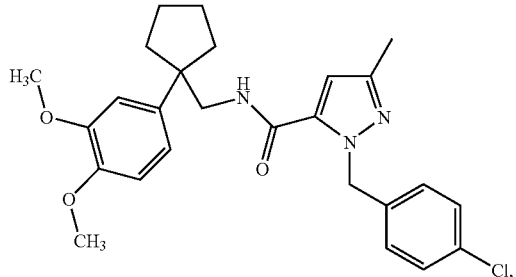

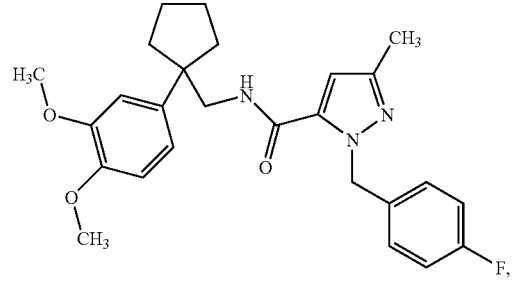

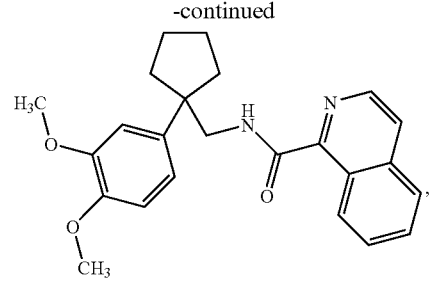

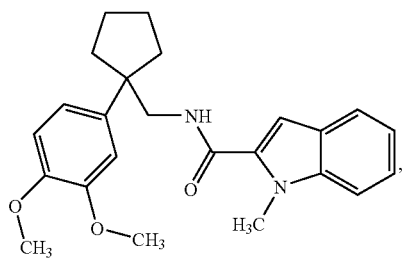

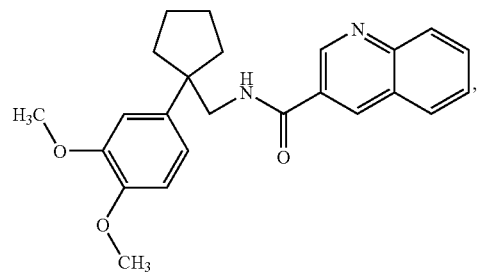

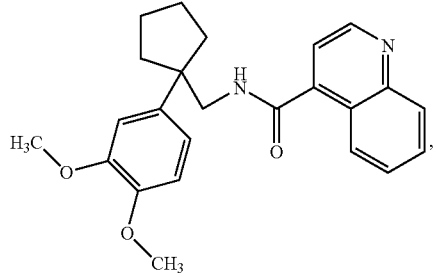

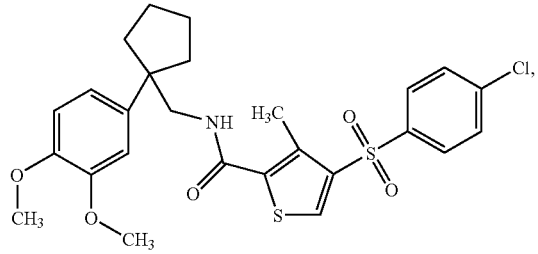

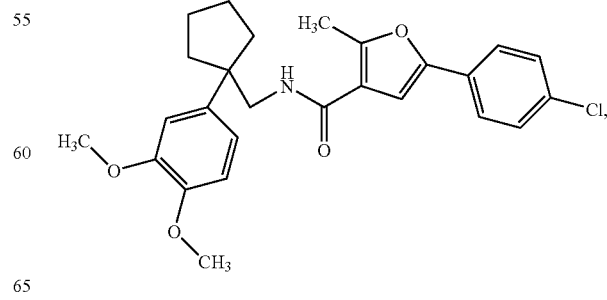

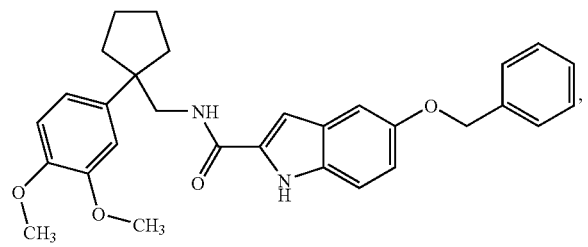
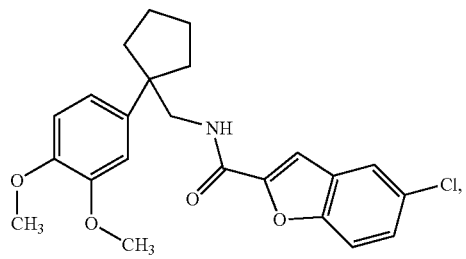
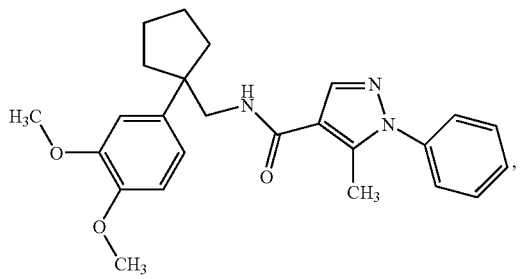
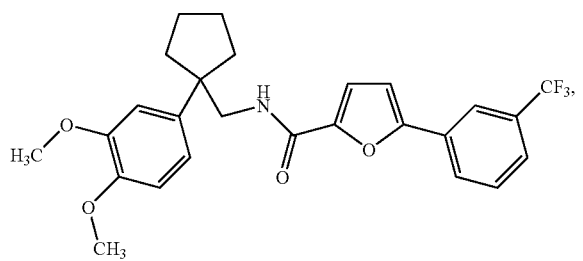
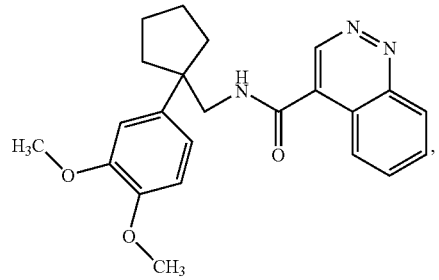
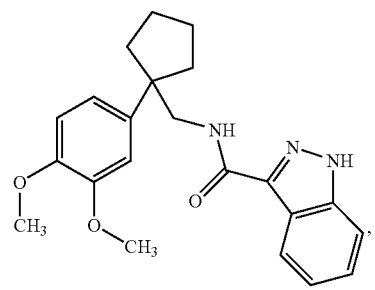
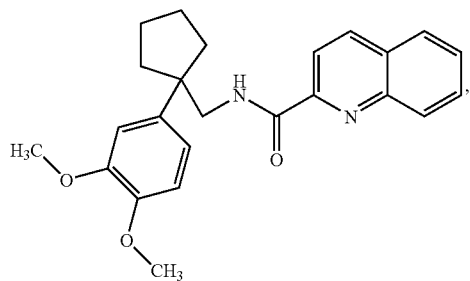
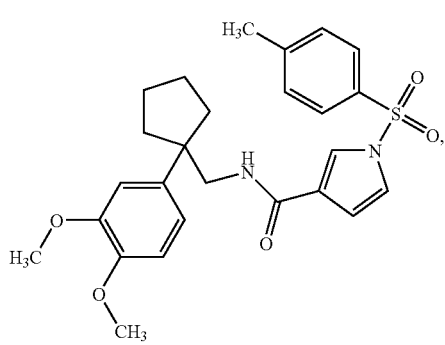
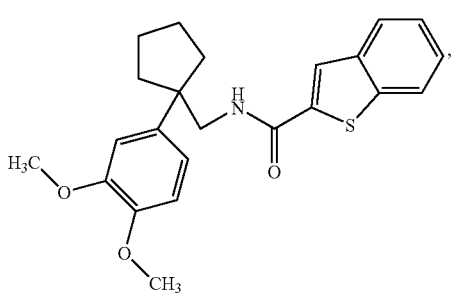
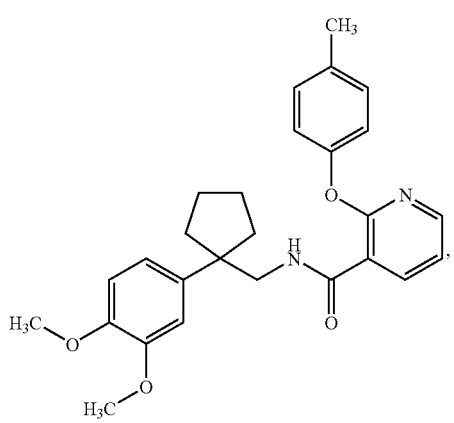
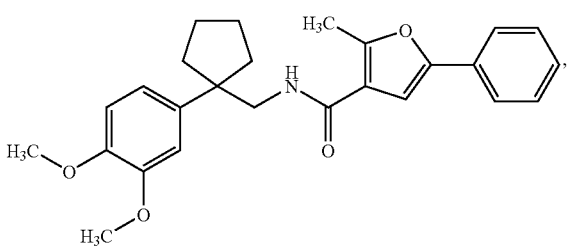

111
-continued
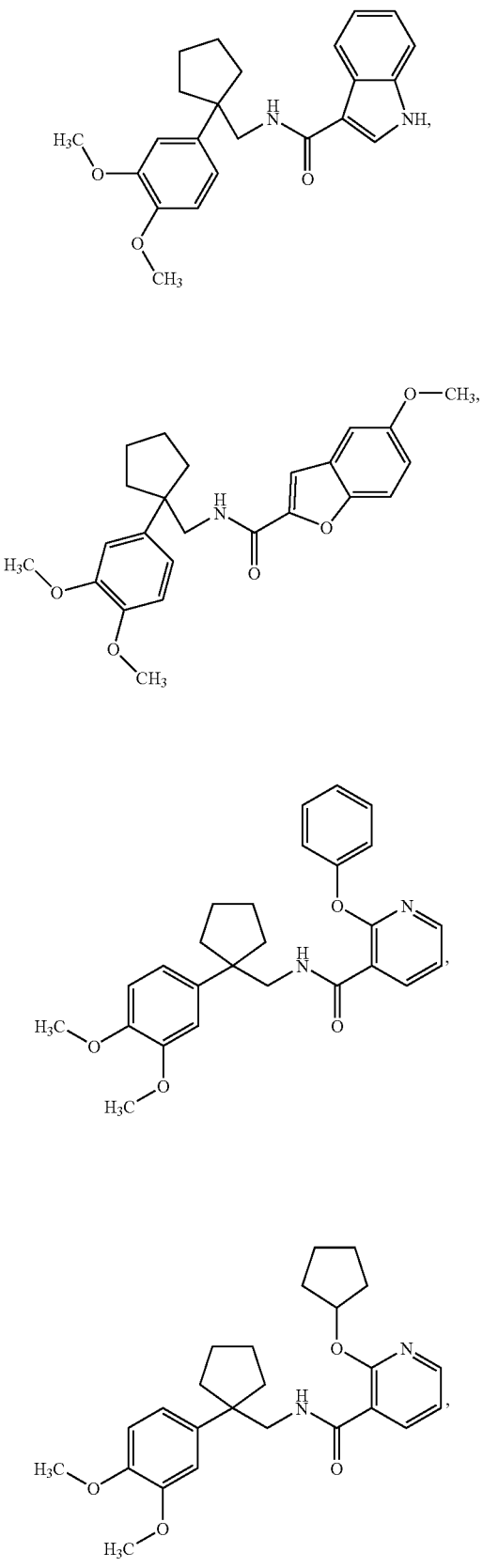
112
-continued
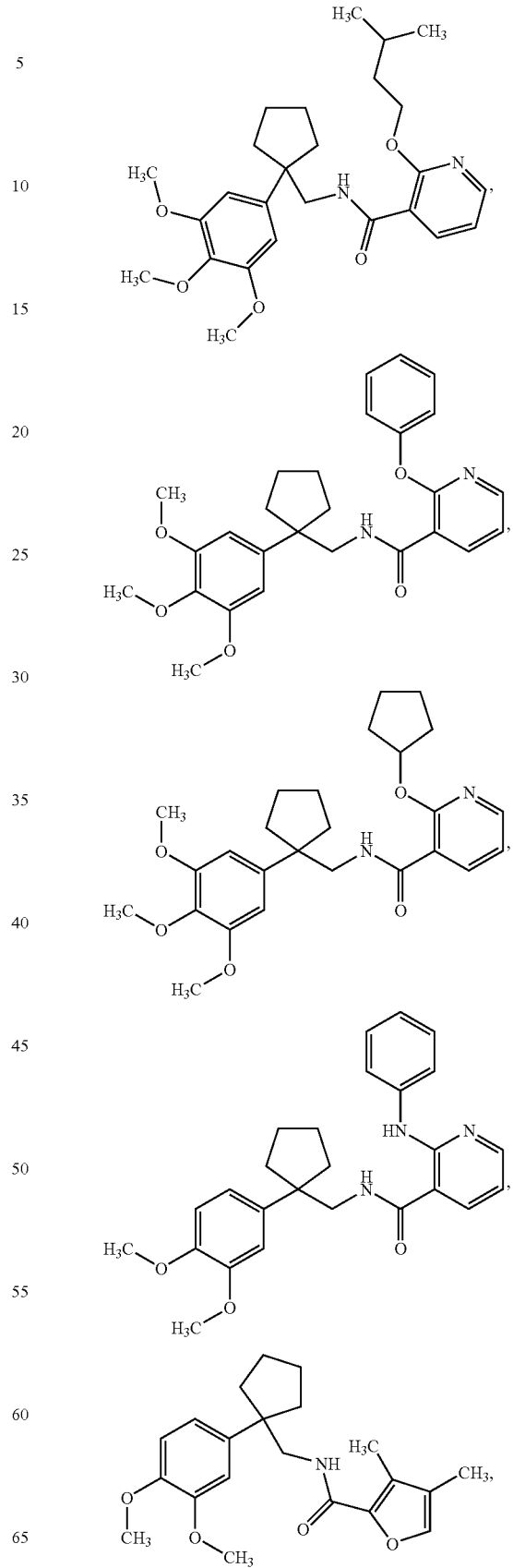

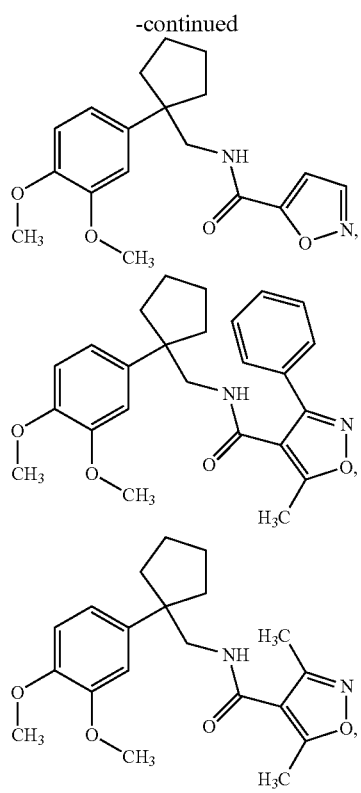
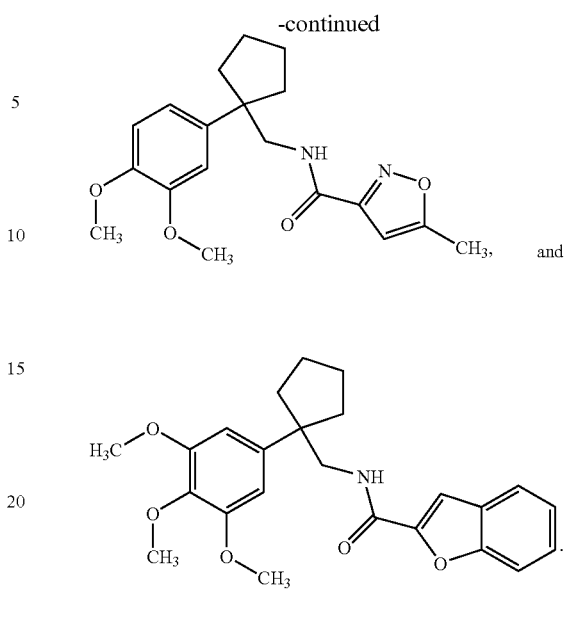
14. A pharmaceutical composition comprising a compound according to any one of claims 1, 2-5, 6, 7, 8, 9, 10, 11, 12 and 13, and a pharmaceutically acceptable carrier.
* * * * *